United States Patent [19]

Birkenmeyer et al.

[11] Patent Number: 5,427,930
[45] Date of Patent: Jun. 27, 1995

[54] AMPLIFICATION OF TARGET NUCLEIC ACIDS USING GAP FILLING LIGASE CHAIN REACTION

[75] Inventors: Larry G. Birkenmeyer, Chicago; John J. Carrino, Gurnee; Bruce J. Dille, Antioch; Hsiang-Yun Hu, Libertyville, all of Ill.; Jon D. Kratochvil, Kenosha, Wis.; Thomas G. Laffler, Libertyville; Ronald L. Marshall, Zion, both of Ill.; Laurie A. Rinehardt, Kenosha, Wis.; Natalie A. Solomon, Buffalo Grove, Ill.

[73] Assignee: Abbott Laboratories, Abbott Park, Ill.

[21] Appl. No.: 722,798

[22] Filed: Jun. 28, 1991

Related U.S. Application Data

[63] Continuation-in-part of Ser. No. 470,674, Jan. 26, 1990, abandoned.

[51] Int. Cl.⁶ .................. C12P 19/34; C12Q 1/68; C07H 21/04
[52] U.S. Cl. .................... 435/91.52; 435/6; 435/91.2; 536/24.32; 536/24.33
[58] Field of Search ............ 435/6, 91, 91.2, 91.52; 536/27, 24.32, 24.33

[56] References Cited

FOREIGN PATENT DOCUMENTS

0185494A2 6/1984 European Pat. Off. .
0246864 11/1987 European Pat. Off. .............. 435/6
0246864A2 11/1987 European Pat. Off. .
0357336A2 3/1990 European Pat. Off. .
WO89/09835 10/1989 WIPO .
8909835 10/1989 WIPO ...................... 435/6

OTHER PUBLICATIONS

Skolnick et al. Genomics 2 273–79 (1988).
Nickerson, *Proceedings of the National Academy of Sciences*, vol. 87, No. 22.

*Primary Examiner*—Mindy B. Fleisher
*Attorney, Agent, or Firm*—Thomas D. Brainard; Lawrence S. Pope

[57] ABSTRACT

An improved, "gap filling" embodiment of the Ligase Chain Reaction (LCR) is described. Gap filling LCR is LCR wherein at least one of the probes is recessed so that a gap is formed between the adjacent probes when they are hybridized to target. The gap is filled using polymerase and deoxyribonucleotide triphosphates before ligation of the probes together. There are single and double gap versions, depending on whether one or two probes are recessed and require filling before ligation. The improvement resides in selecting and using target sequences such that only a single type, or two types, of deoxyribonucleotide triphosphate(s) are required to fill double gaps each being 1–10 bases in length, preferably 1–3 bases. Probes having specific sequences are claimed for a number of pathogens.

30 Claims, 2 Drawing Sheets

SEQUENCE LISTING ( 1 ) GENERAL INFORMATION:

( i i i ) NUMBER OF SEQUENCES: 124

( 2 ) INFORMATION FOR SEQ ID NO: 1:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 1:

AACCCTTTAG AGACTATGTA GACC                        24

( 2 ) INFORMATION FOR SEQ ID NO: 2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 2:

TCTACATAGT CTCTAAAGGG TTC                         23

( 2 ) INFORMATION FOR SEQ ID NO: 3:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 3:

TTCTATAAAA CTCTAAGAGC CGA                         23

( 2 ) INFORMATION FOR SEQ ID NO: 4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 4:

CGGCTCTTAG AGTTTTATAG AACC                       24

( 2 ) INFORMATION FOR SEQ ID NO: 5:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 5:

AGAACGATTC GCAGTCAATC CTGG 24

( 2 ) INFORMATION FOR SEQ ID NO: 6:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 6:

AGGATTGACT GCGAATCGTT CTA 23

( 2 ) INFORMATION FOR SEQ ID NO: 7:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 7:

TGTTAGAAAC ATCAGAAGGC TGC 23

( 2 ) INFORMATION FOR SEQ ID NO: 8:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 8:

CAGCCTTCTG ATGTTTCTAA CAGG 24

( 2 ) INFORMATION FOR SEQ ID NO: 9:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 9:

GCTAATTTTT TAGGGAAGAT CTGG 24

( 2 ) INFORMATION FOR SEQ ID NO: 10:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 10:

AGATCTTCCC TAAAAAATTA GCC 23

( 2 ) INFORMATION FOR SEQ ID NO: 11:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 11:

TTCCTACAAG GGAACGCCAG GGA                                        2 3

( 2 ) INFORMATION FOR SEQ ID NO: 12:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 12:

CCCTGGCGTT CCCTTGTAGG AAGG                                      2 4

( 2 ) INFORMATION FOR SEQ ID NO: 13:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 13:

GATGGGTGCG AGAGCGTCGG TATT                                      2 4

( 2 ) INFORMATION FOR SEQ ID NO: 14:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 14:

TACCGACGCT CTCGCACCCA TCT                                        2 3

( 2 ) INFORMATION FOR SEQ ID NO: 15:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 15:

GCGGGGGAGA ATTAGATAAA TGG                                        2 3

( 2 ) INFORMATION FOR SEQ ID NO: 16:

( i ) SEQUENCE CHARACTERISTICS:
        ( A ) LENGTH: 24
        ( B ) TYPE: nucleic acid
        ( C ) STRANDEDNESS: single ( D ) TOPOLOGY: linear ( i i ) MOLECULE TYPE: Other nucleic acid (synthetic DNA)

( x i ) SEQUENCE DESCRIPTION: SEQ ID NO: 16:

CATTTATCTA ATTCTCCCCC GCTT                                                                 24

( 2 ) INFORMATION FOR SEQ ID NO: 17:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 17:

ACCCACTGCT TAAGCCTCAA TAAAG                                                                25

( 2 ) INFORMATION FOR SEQ ID NO: 18:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 18:

TTTATTGAGG CTTAAGCAGT GGGTT                                                                25

( 2 ) INFORMATION FOR SEQ ID NO: 19:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 19:

TTGCCTTGAG TGCTTCAAGT AGTGT                                                                25

( 2 ) INFORMATION FOR SEQ ID NO: 20:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 20:

CACTACTTGA AGCACTCAAG GCAAG                                                                25

( 2 ) INFORMATION FOR SEQ ID NO: 21:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 21:

GAACAAGCCC CAGAAGACCA AGGG                                                                 24

( 2 ) INFORMATION FOR SEQ ID NO: 22:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 22:

TTGGTCTTCT GGGGCTTGTT C        21

( 2 ) INFORMATION FOR SEQ ID NO: 23:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 23:

ACAGAGGGAG CCATACAATG AA        22

( 2 ) INFORMATION FOR SEQ ID NO: 24:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 24:

TTCATTGTAT GGCTCCCTCT GTGG        24

( 2 ) INFORMATION FOR SEQ ID NO: 25:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 25:

GCATGCAGGG CCTATTGCAC CAGG        24

( 2 ) INFORMATION FOR SEQ ID NO: 26:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 26:

TGGTGCAATA GGCCCTGCAT G        21

( 2 ) INFORMATION FOR SEQ ID NO: 27:

( i ) SEQUENCE CHARACTERISTICS:
        ( A ) LENGTH: 22
        ( B ) TYPE: nucleic acid (C) STRANDEDNESS: single
    (D) TOPOLOGY: linear (ii) MOLECULE TYPE: Other nucleic acid (synthetic DNA)

(xi) SEQUENCE DESCRIPTION: SEQ ID NO: 27:

AAATGAGAGA ACCAAGGGGA AG                                            22

(2) INFORMATION FOR SEQ ID NO: 28:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 28:

ACTTCCCCTT GGTTCTCTCA TTTGG                                         25

(2) INFORMATION FOR SEQ ID NO: 29:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 29:

AGAAATCTAT AAAAGATGGA TAAT                                          24

(2) INFORMATION FOR SEQ ID NO: 30:

(i) SEQUENCE CHARACTERISTICS:
        (A) LENGTH: 23
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 30:

TTATCCATCT TTTATAGATT TCT                                           23

(2) INFORMATION FOR SEQ ID NO: 31:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 31:

TGGGATTAAA TAAAATAGTA AG                                            22

(2) INFORMATION FOR SEQ ID NO: 32:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 32:

CTTACTATTT TATTTAATCC CAGG 24

(2) INFORMATION FOR SEQ ID NO: 33:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 33:

GCATTAGGAA TCATTCAAGC ACAA 24

(2) INFORMATION FOR SEQ ID NO: 34:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 34:

GTGCTTGAAT GATTCCTAAT GC 22

(2) INFORMATION FOR SEQ ID NO: 35:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 35:

AGATAAGAGT GAATCAGAGT TA 22

(2) INFORMATION FOR SEQ ID NO: 36:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 36:

TAACTCTGAT TCACTCTTAT CTGG 24

(2) INFORMATION FOR SEQ ID NO: 37:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 37:

AAGGAAGGGA AAATTTCAAA AATT 24

(2) INFORMATION FOR SEQ ID NO: 38:

(i) SEQUENCE CHARACTERISTICS:
        (A) LENGTH: 22

(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 38:

TTTTTGAAAT TTTCCCTTCC TT    22

(2) INFORMATION FOR SEQ ID NO: 39:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 39:

CCTGAAAATC CATACAATAC T    21

(2) INFORMATION FOR SEQ ID NO: 40:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 40:

AGTATTGTAT GGATTTTCAG GCCC    24

(2) INFORMATION FOR SEQ ID NO: 41:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 41:

AACCTTGTTG GTCCAAAATG CAAA    24

(2) INFORMATION FOR SEQ ID NO: 42:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 42:

GCATTTTGGA CCAACAAGGT T    21

(2) INFORMATION FOR SEQ ID NO: 43:

(i) SEQUENCE CHARACTERISTICS:
(A) LENGTH: 21
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 43:

AGATTGTAAG ACTATTTTAA A                                                 21

( 2 ) INFORMATION FOR SEQ ID NO: 44:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 44:

TTTAAAATAG TCTTACAATC TGGG                                              24

( 2 ) INFORMATION FOR SEQ ID NO: 45:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 45:

GTAATATGGG GAAAGACTCC TAAA                                              24

( 2 ) INFORMATION FOR SEQ ID NO: 46:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 46:

AGGAGTCTTT CCCCATATTA C                                                 21

( 2 ) INFORMATION FOR SEQ ID NO: 47:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 47:

AAACTACCCA TACAAAAGGA A                                                 21

( 2 ) INFORMATION FOR SEQ ID NO: 48:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 48:

TTCCTTTTGT ATGGGTAGTT TAAA                                              24

( 2 ) INFORMATION FOR SEQ ID NO: 49:

( i ) SEQUENCE CHARACTERISTICS:

(A) LENGTH: 24
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 49:

GACAGAGGAC TTGCTGCACC TCAA 24

(2) INFORMATION FOR SEQ ID NO: 50:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 50:

GAGGTGCAGC AAGTCCTCTG TCG 23

(2) INFORMATION FOR SEQ ID NO: 51:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 51:

CTCTCTTTGG AAAAGACCAG TAG 23

(2) INFORMATION FOR SEQ ID NO: 52:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 52:

TACTGGTCTT TTCCAAAGAG AGAA 24

(2) INFORMATION FOR SEQ ID NO: 53:

(i) SEQUENCE CHARACTERISTICS:
(A) LENGTH: 24
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 53:

ATCACCACAG AACAAGAAAT ACAA 24

(2) INFORMATION FOR SEQ ID NO: 54:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: Other nucleic acid (synthetic DNA)

( x i ) SEQUENCE DESCRIPTION: SEQ ID NO: 54:

GTATTTCTTG TTCTGTGGTG ATC 23

( 2 ) INFORMATION FOR SEQ ID NO: 55:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 55:

CCTCCAAGCA AAAAATTCAA AAT 23

( 2 ) INFORMATION FOR SEQ ID NO: 56:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 56:

TTTTGAATTT TTTGCTTGGA GGAA 24

( 2 ) INFORMATION FOR SEQ ID NO: 57:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 57:

CTATGATATT AATCAAATGC TTAA 24

( 2 ) INFORMATION FOR SEQ ID NO: 58:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 58:

AAGCATTTGA TTAATATCAT AGG 23

( 2 ) INFORMATION FOR SEQ ID NO: 59:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 59:

GTGTGGGCGA CCATCAAGCA GCG 23

( 2 ) INFORMATION FOR SEQ ID NO: 60:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 60:

GCTGCTTGAT GGTCGCCCAC ACAA    24

( 2 ) INFORMATION FOR SEQ ID NO: 61:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 61:

TTTAGAGCCC CAAAATGAAA TTCC    24

( 2 ) INFORMATION FOR SEQ ID NO: 62:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 62:

AATTTCATTT TGGGGCTCTA AA    22

( 2 ) INFORMATION FOR SEQ ID NO: 63:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 63:

TTGACCTTCT ATGTCACGAG    20

( 2 ) INFORMATION FOR SEQ ID NO: 64:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 64:

CTCGTGACAT AGAAGGTCAA CC    22

( 2 ) INFORMATION FOR SEQ ID NO: 65:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 65:

ATAATATAAG GGGTCGGTGG ACC                                    23

( 2 ) INFORMATION FOR SEQ ID NO: 66:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 66:

TCCACCGACC CCTTATATTA T                                      21

( 2 ) INFORMATION FOR SEQ ID NO: 67:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 67:

TCGATGTATG TCTTGTTGCA GA                                     22

( 2 ) INFORMATION FOR SEQ ID NO: 68:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 68:

TCTGCAACAA GACATACATC GACC                                   24

( 2 ) INFORMATION FOR SEQ ID NO: 69:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 69:

CAACATAGCT GGGCACTATA GAGG                                   24

( 2 ) INFORMATION FOR SEQ ID NO: 70:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 70:

TCTATAGTGC CCAGCTATGT TG                                     22

( 2 ) INFORMATION FOR SEQ ID NO: 71:

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( x i ) SEQUENCE DESCRIPTION: SEQ ID NO: 71:

AGTGCCATTC GTGCTGCAAC C      21

( 2 ) INFORMATION FOR SEQ ID NO: 72:

( i ) SEQUENCE CHARACTERISTICS:
  ( A ) LENGTH: 23
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( x i ) SEQUENCE DESCRIPTION: SEQ ID NO: 72:

GGTTGCAGCA CGAATGGCAC TGG      23

( 2 ) INFORMATION FOR SEQ ID NO: 73:

( i ) SEQUENCE CHARACTERISTICS:
  ( A ) LENGTH: 26
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( x i ) SEQUENCE DESCRIPTION: SEQ ID NO: 73:

TTTGTTGGGG TAATCAATTA TTTGTT      26

( 2 ) INFORMATION FOR SEQ ID NO: 74:

( i ) SEQUENCE CHARACTERISTICS:
  ( A ) LENGTH: 24
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( x i ) SEQUENCE DESCRIPTION: SEQ ID NO: 74:

CAAATAATTG ATTACCCCAA CAAA      24

( 2 ) INFORMATION FOR SEQ ID NO: 75:

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( x i ) SEQUENCE DESCRIPTION: SEQ ID NO: 75:

CTGTGGTTGA TACCACACGC A      21

( 2 ) INFORMATION FOR SEQ ID NO: 76:

( i ) SEQUENCE CHARACTERISTICS:
  ( A ) LENGTH: 22
  ( B ) TYPE: nucleic acid
  ( C ) STRANDEDNESS: single
  ( D ) TOPOLOGY: linear (i i) MOLECULE TYPE: Other nucleic acid (synthetic DNA)

(x i) SEQUENCE DESCRIPTION: SEQ ID NO: 76:

TGCGTGTGGT ATCAACCACA GT 22

(2) INFORMATION FOR SEQ ID NO: 77:

(i) SEQUENCE CHARACTERISTICS:
        (A) LENGTH: 23
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 77:

CCCCCTGTTC TGGTTCCTAA CGG 23

(2) INFORMATION FOR SEQ ID NO: 78:

(i) SEQUENCE CHARACTERISTICS:
        (A) LENGTH: 23
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 78:

GTTAGGAACC AGAACAGTGG GGA 23

(2) INFORMATION FOR SEQ ID NO: 79:

(i) SEQUENCE CHARACTERISTICS:
        (A) LENGTH: 22
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 79:

TCCCCTGCTC TAGATATCCT CT 22

(2) INFORMATION FOR SEQ ID NO: 80:

(i) SEQUENCE CHARACTERISTICS:
        (A) LENGTH: 23
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 80:

GAGGATATCT AGAGCAGGGG AGG 23

(2) INFORMATION FOR SEQ ID NO: 81:

(i) SEQUENCE CHARACTERISTICS:
        (A) LENGTH: 23
        (B) TYPE: nucleic acid
        (C) STRANDEDNESS: single
        (D) TOPOLOGY: linear (i i) MOLECULE TYPE: Other nucleic acid (synthetic DNA)

(x i) SEQUENCE DESCRIPTION: SEQ ID NO: 81:

TATGACAGCT TTAGCGCCGT CAG 23

( 2 ) INFORMATION FOR SEQ ID NO: 82:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 82:

TGACGGCGCT AAAGCTGCAT AG        22

( 2 ) INFORMATION FOR SEQ ID NO: 83:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 83:

GAGGATAACC TGGGGTTCCT GAT        23

( 2 ) INFORMATION FOR SEQ ID NO: 84:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 84:

TCAGGAACCC CAGGTTATCC TCG        23

( 2 ) INFORMATION FOR SEQ ID NO: 85:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 85:

TTTTACTTGC AAGACATTCC TCAGG        25

( 2 ) INFORMATION FOR SEQ ID NO: 86:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 86:

TGAGGAATGT CTTGCAAGTA AAAGC        25

( 2 ) INFORMATION FOR SEQ ID NO: 87:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 87:

ATTAATTGCT ACAGGACATC TTGTC    25

( 2 ) INFORMATION FOR SEQ ID NO: 88:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 88:

CAAGATGTCC TGTAGCAATT AATGG    25

( 2 ) INFORMATION FOR SEQ ID NO: 89:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 89:

GGGAATCCTG CTGAACCAAG    20

( 2 ) INFORMATION FOR SEQ ID NO: 90:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 90:

TTGGTTCAGC AGGATTCCC    19

( 2 ) INFORMATION FOR SEQ ID NO: 91:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 91:

TTATGATCGA CGGAATTCTG TG    22

( 2 ) INFORMATION FOR SEQ ID NO: 92:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 92:

CACAGAATTC CGTCGATCAT AAGG    24

( 2 ) INFORMATION FOR SEQ ID NO: 93:

( i ) SEQUENCE CHARACTERISTICS:
      ( A ) LENGTH: 22
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 93:

GATACTTCGC ATCATGTGTT CC                          22

( 2 ) INFORMATION FOR SEQ ID NO: 94:

( i ) SEQUENCE CHARACTERISTICS:
      ( A ) LENGTH: 20
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 94:

AACACATGAT GCGAAGTATC                             20

( 2 ) INFORMATION FOR SEQ ID NO: 95:

( i ) SEQUENCE CHARACTERISTICS:
      ( A ) LENGTH: 23
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 95:

AGTTTCTTTG TCCTCCTATA ACG                         23

( 2 ) INFORMATION FOR SEQ ID NO: 96:

( i ) SEQUENCE CHARACTERISTICS:
      ( A ) LENGTH: 25
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 96:

CGTTATAGGA GGACAAAGAA ACTCC                       25

( 2 ) INFORMATION FOR SEQ ID NO: 97:

( i ) SEQUENCE CHARACTERISTICS:
      ( A ) LENGTH: 22
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 97:

AATATTTGCG CGGCGGGGAC GG                          22

( 2 ) INFORMATION FOR SEQ ID NO: 98:

( i ) SEQUENCE CHARACTERISTICS:
      ( A ) LENGTH: 20
      ( B ) TYPE: nucleic acid
      ( C ) STRANDEDNESS: single -continued ( D ) TOPOLOGY: linear ( i i ) MOLECULE TYPE: Other nucleic acid (synthetic DNA)

( x i ) SEQUENCE DESCRIPTION: SEQ ID NO: 98:

GTCCCCGCCG CGCAAATATT                                        20

( 2 ) INFORMATION FOR SEQ ID NO: 99:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 99:

TGCCCTAATA TTAAGAAAT AGGTT                             25

( 2 ) INFORMATION FOR SEQ ID NO: 100:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 100:

AACCTATTTC TTTAATATTA GGGCAG                          26

( 2 ) INFORMATION FOR SEQ ID NO: 101:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 101:

GCCATATTGT GTTGAAACAC CGCCC                             25

( 2 ) INFORMATION FOR SEQ ID NO: 102:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 102:

CGGTGTTTCA ACACAATATG GC                                   22

( 2 ) INFORMATION FOR SEQ ID NO: 103:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 103:

AACCCGATAT AATCCGCCCT T                                    21

( 2 ) INFORMATION FOR SEQ ID NO: 104:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 104:

AAGGGCGGAT TATATCGGGT TCC                                                23

( 2 ) INFORMATION FOR SEQ ID NO: 105:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 105:

CAACATCAGT GAAAATCTTT TTTTAACC                                        28

( 2 ) INFORMATION FOR SEQ ID NO: 106:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 106:

TTAAAAAAG ATTTTCACTG ATGTTG                                        26

( 2 ) INFORMATION FOR SEQ ID NO: 107:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 107:

TCAAACCGAA TAAGGAGCCG A                                                  21

( 2 ) INFORMATION FOR SEQ ID NO: 108:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 108:

TTCGGCTCCT TATTCGGTTT GACC                                            24

( 2 ) INFORMATION FOR SEQ ID NO: 109:

( i ) SEQUENCE CHARACTERISTICS:
        ( A ) LENGTH: 24
        ( B ) TYPE: nucleic acid ( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 109:

TGATGCCAGC TGAGGCAAAT TAGG 24

( 2 ) INFORMATION FOR SEQ ID NO: 110:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 110:

TAATTTGCCT CAGCTGGCAT CA 22

( 2 ) INFORMATION FOR SEQ ID NO: 111:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 111:

TTAAATTTCA AATAAATCAA GCGGTA 26

( 2 ) INFORMATION FOR SEQ ID NO: 112:

( i ) SEQUENCE CHARACTERISTICS:
( A ) LENGTH: 28
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 112:

TACCGCTTGA TTTATTTGAA ATTTAAGG 28

( 2 ) INFORMATION FOR SEQ ID NO: 113:

( i ) SEQUENCE CHARACTERISTICS:
( A ) LENGTH: 20
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 113:

CGGGCGGGGT CGTCCGTTCC 20

( 2 ) INFORMATION FOR SEQ ID NO: 114:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 114:

AACGGACGAC CCCGCCCG                                              18

( 2 ) INFORMATION FOR SEQ ID NO: 115:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 115:

TGGAAATAAT ATATCGATT                                              19

( 2 ) INFORMATION FOR SEQ ID NO: 116:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 116:

AATCGATATA TTATTTCCAC C                                           21

( 2 ) INFORMATION FOR SEQ ID NO: 117:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 117:

AAAACGAAGA TACTAAATCT GTAA                                        24

( 2 ) INFORMATION FOR SEQ ID NO: 118:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 118:

ACAGATTTAG TATCTTCGTT TT                                          22

( 2 ) INFORMATION FOR SEQ ID NO: 119:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 119:

GCAGAAACAC CTTTTGAATT AA                                          22

( 2 ) INFORMATION FOR SEQ ID NO: 120:

( i ) SEQUENCE CHARACTERISTICS:
        ( A ) LENGTH: 24

(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 120:

TTAATTCAAA AGGTGTTTCT GCAA            24

(2) INFORMATION FOR SEQ ID NO: 121:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 121:

CATCTTTTGG AGCTAAATAT AAG             23

(2) INFORMATION FOR SEQ ID NO: 122:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 122:

TTATATTTAG CTCCAAAAGA TGC             23

(2) INFORMATION FOR SEQ ID NO: 123:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 123:

TTGGATTAAC AAAAATAAAC GAT             23

(2) INFORMATION FOR SEQ ID NO: 124:

(i) SEQUENCE CHARACTERISTICS:
(A) LENGTH: 23
(B) TYPE: nucleic acid
(C) STRANDEDNESS: single
(D) TOPOLOGY: linear (ii) MOLECULE TYPE: Other nucleic acid (synthetic DNA)

(xi) SEQUENCE DESCRIPTION: SEQ ID NO: 124:

TCGTTTATTT TTGTTAATCC AAG             23

AMPLIFICATION OF TARGET NUCLEIC ACIDS USING GAP FILLING LIGASE CHAIN REACTION

This application is a continuation-in-part of co-owned application Ser. No. 07/470,674, filed Jan. 26, 1990, abandoned. It is also related to application Ser. No. 07/634,771, filed Jan. 9, 1991, which is also a continuation-in-part of said 470,674 application. The entire disclosures of both applications are incorporated herein by reference.

BACKGROUND

This invention relates to a method of performing ligase chain reaction (LCR) amplification and, particularly, to a method of ligase chain reaction amplification wherein at least one of the probes is reversibly modified at the intended point of ligation so that it is not a substrate for the ligase catalyzed reaction. Exemplary modifications include the absence of one or more nucleic acid bases to form a "recess". The modified end prevents or reduces target independent blunt-end ligation of probe duplexes and is later corrected in a target dependent manner to enable ligation.

In many cases, the feasibility of a nucleic acid based diagnostic assay is dependent on the ability to amplify the signal generated by only a few molecules of target. Although signal amplification is one potential solution, target amplification is often the preferred solution in nucleic acid based assays. Target amplification involves the repeated copying or duplication of sections of the nucleic acid designated as the target.

In the target amplification technique known as polymerase chain reaction (PCR) a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to increase geometrically the number of target sequence molecules. PCR is described further in U.S. Pat. Nos. 4,683,195 and 4,683,202.

An alternate mechanism for target amplification is known as ligase chain reaction (LCR). In LCR, two primary (first and second probes) and two secondary (third and fourth) probes are employed in excess. The first probe hybridizes to a first segment of the target strand and the second probe hybridizes to a second segment of the target strand, the first and second segments being contiguous so that the primary probes abut one another in 5' phosphate-3' hydroxyl relationship and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes will also hybridize to the target complement in the first instance. Once the fused strand of primary probes is separated from the target strand, it will hybridize with the third and fourth probes which can be ligated to form a complementary, secondary fused product. In order to understand LCR and the improvements described herein, it is important to realize that the fused products are functionally equivalent to either the target or its complement. By repeated cycles of hybridization and ligation, amplification of the target sequence is achieved. This technique is described more completely in EP-A-320 308, the entire disclosure of which is incorporated herein by reference.

A potential problem associated with ligase chain reaction is background signal caused by target independent ligation of the probes. Since the third probe hybridizes to the first probe and the fourth probe hybridizes to the second probe, the probes, which are added in excess, can easily form duplexes among themselves. These duplexes can become ligated independently of the presence of target to form a fused product which is then indistinguishable from the desired amplified target, yet which is still capable of supporting further amplification. Although target independent blunt-end ligation of these duplexes is a relatively rare event, it is sufficiently common to cause undesirably high background signals in diagnostic assays.

Some attempts to overcome this background problem have been published. For example, WO 90/01069 (Segev Diagnostics) and GB 2 225 112 A (Imperial Chemical Industries Plc.) describe versions of a ligation-based amplification scheme which includes a polymerase-mediated gap-filling step prior to ligation. However, these references teach nothing about selection of the particular target sequences as taught and claimed in the present application.

It is therefore a primary object of the present invention to improve the sensitivity of nucleic acid based assays by decreasing the occurrence of target independent ligation which causes falsely positive background signal. This object is met in the present invention by modifying at least one probe end so that when hybridized with its complementary probe, the resulting duplex is not "blunt-ended" (i.e. ligatable) with respect to the partner complementary probe duplexes. After hybridizing to the target, the modified ends are "corrected" in a target dependent fashion to render the adjacent probes ligatable. Several features of the probes and the associated target sequences taught in this application make this task particularly elegant.

According to one feature, the probes have recesses relative to the point of ligation which create a gap when hybridized to the target. The gap is then filled in a target dependent manner to render the probes ligatable. Gap filling can be accomplished by extension of one or more probes, preferably two probes. Targets are selected and probes are designed so that only one, or a maximum of two, of the four deoxyribonucleotide triphosphates is needed to fill both the gaps.

SUMMARY OF THE INVENTION

In a first aspect, the invention relates to a method for detecting the presence of a target nucleic acid sequence in a sample, said method employing the ligase chain reaction to create geometrically increasing numbers of reorganized probe molecules in the presence of said target sequence, said method comprising:

a) providing a sample suspected to contain nucleic acid, the nucleic acid having a target sequence of the formula:

wherein E represents any base, F represents any base except E, p and q are independently integers from 1 to about 10, X represents any base except E or F', Z represents any base except F or E', N represents any base, and h and k are independently integers from 5 to 100, provided the sums (p+h) and (q+k) each are greater than 10, wherein $(N)_h$ and $(N)_k$ represent sequences that are characteristic for the target sought to be detected;

b) providing a plurality of each of four probes having the formulas:

| | |
|---|---|
| 5'-$(N)_h$  X $E_p$-3' | A |
| 3'-$(N')_h$  X'-5' | A' |
| 5'-$(N)_k$  -3' | B |
| 3'-$F'_q Z'(N')_k$  -5' | B' | wherein the symbols have the same meanings given above, except that h and k need only approximate h and k, respectively, varying by no more than 25%, and wherein at least one of the probes is labeled with a moiety capable of detection; and also providing deoxyribonucleotide triphosphates of E' and F, a polymerase reagent and a ligase reagent;

c) performing the following cycle at least once:
  i) mixing said probes with said sample under hybridizing conditions to allow probes to hybridize to the target sequence and its complement if present, or to reorganized probes created therefrom;
  ii) using target sequence or reorganized probes created therefrom as template, extending probe A with said polymerase reagent by adding F deoxyribonucleotide triphosphates to its 3' end, and extending probe B' with said polymerase reagent by adding E' deoxyribonucleotide triphosphates to its 3' end
  iii) ligating extended probe A to probe B, and extended probe B' to probe A', using said ligase reagent to form reorganized probe molecules; and
  iv) providing denaturing conditions to separate said reorganized probe molecules from said template;

d) separating reorganized probe molecules from unreorganized labeled probes; and e) detecting the presence of said label in the reorganized or fraction as a measure of the presence of the target sequence.

In especially preferred embodiments, F is E' so that both gaps can be filled by the deoxyribonucleotide triphosphate of only E'. Preferably p and q are small, i.e., between 1 and 3, inclusive. Integers p and q may be equal or may differ by one or more. Preferably, the label comprises one or more haptens covalently bound to at least one of the probes.

In another aspect, the invention relates to diagnostic kits for the detection of a target nucleic acid sequence in a sample, said nucleic acid having a target sequence comprising 5'-$(N)_h X E_p F_p Z(N)_k$-3' wherein E and F independently represent any base, p and q are independently integers from 1 to about 10, X represents any base except E or F', Z represents any base except F or E', N represents any base, and h and k are independently integers from 5 to 100, provided the sums (p+h) and (q+k) each are greater than 10, wherein $(N)_h$ and $(N)_k$ represent sequences that are characteristic for the target sought to be detected, said kit comprising in combination:

(a) four probes, having the formulas:

| | |
|---|---|
| 5'-$(N)_h$  X $E_p$-3' | A |
| 3'-$(N')_h$  X'-5' | A' |
| 5'-Z$(N)_k$  -3' | B |
| 3+-$F'_q Z'(N')_k$  -5' | B' | wherein the symbols have the same meanings given above, except that h and k need only approximate h and k, respectively, varying by no more than 25%, and wherein at least one of the probes is labeled with a moiety capable of detection;

(b) a polymerase reagent capable of extending probe A with said polymerase reagent in a target dependent manner by adding F deoxyribonucleotide triphosphates to its 3' end, and extending probe B' with said polymerase reagent in a target dependent manner by adding E' deoxyribonucleotide triphosphates to its 3' end, thereby to render the primary probes ligatable to one another when hybridized to target and, optionally, to render the secondary probes ligatable to one another when hybridized to target;

(c) deoxyribonucleotide triphosphates of E' and F; and (d) a ligase reagent for ligating the extended probe A to probe B, and extended probe B' to probe A', thereby to form reorganized probe molecules.

Especially preferred kits, also include means for separating reorganized probe molecules from unreorganized labeled probes and/or means for detecting the detectable label.

In yet another aspect, the invention relates to compositions of matter each comprising a mixture of four probes, the four probes being selected from specific sets of sequences given in the examples. These compositions of matter have utility in detecting the presence of certain pathogens according to the methods described above. It will, of course, be realized that sequences being slightly shorter or longer than the exemplified and claimed sequences are deemed to fall within the scope of the invention, provided they are capable of hybridizing with the same locations on the targets as the claimed sequences.

DETAILED DESCRIPTION

Figure 1:
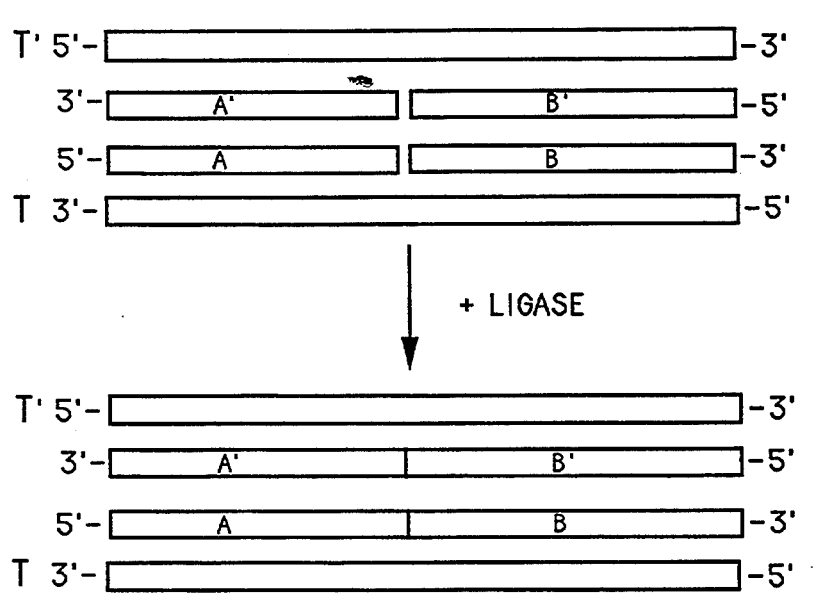
FIG. 1 is a graphic representation of the process of ligase chain reaction as it is known in the prior art.

For purposes of this invention, the target sequence is described to be single stranded. However, this should be understood to include the case where the target is actually double stranded but is simply separated from its complement prior to hybridization with the probes. In the case of double stranded target, the third and fourth (secondary) probes, A' and B', respectively, will participate in the initial step by hybridizing to the target complement. In the case of single stranded target, they will not participate in the initial hybridization step, but will participate in subsequent hybridization steps, combining with the primary fused sequence produced by ligating the first and second probes. Target sequences may comprise deoxyribonucleic acid (DNA) or ribonucleic acid (RNA).

Target sequences may be the nucleic acid of virtually any entity which contains nucleic acid. For example, but not limitation, the bacteria and viruses illustrated in the examples have nucleic acid target sequences. Target sequences may, but need not, represent pathogenic organisms or viruses. Target sequences may also represent nucleic acid which is being examined for the presence of a specific allele, or for a specific mutation of deletion, such as is often the case in genetic testing. Finally, target sequences may be simply any nucleic acid sequence of general interest, such as may be the case in forensic analysis of DNA.

Throughout this application, the "prime" (') designation is used to indicate a complementary base or sequence. A probe is "complementary" to another probe if it hybridizes to the other probe and has substantially complementary base pairs in the hybridized region. Thus, probe A can be complementary to A' even though it may have ends not coterminal with A'. The same is true of B and B'. Similarly, the short sequences $X_n$ and $Y_m$ have complementary sequences designated as $X'_n$ and $Y'_m$, respectively. Finally, the complement of a single base, e.g. Q, is designated as Q'. As used herein with respect to sequences, "complementary" encompasses sequences that have mismatched base pairs in the hybridizable region, provided they can be made to hybridize under assay conditions.

It is also to be understood that the term "the 4 bases" shall refer to Guanine (G), Cytosine (C), Adenine (A) and Thymine (T) when the context is that of DNA; but shall refer to Guanine (G), Cytosine (C), Adenine (A) and Uracil (U) in the context of RNA. The term also includes analogs and derivatives of the bases named above. Although the degenerate base Inosine (I) may be employed with this invention, it is not preferred to use I within modified portions of the probes according to the invention.

It is an important feature of the present invention that instead of using two pairs of probes capable of forming blunt-ended duplexes, at least one probe of one of the probe pairs initially includes a "modified" end which renders the resultant duplex "nonblunt" and/or not a suitable substrate for the ligase catalyzed fusion of the two probe duplexes. A "modified end" is defined with respect to the point of ligation rather than with respect to its complementary probe. A "modified end" has omitted bases to create a "gap" between one probe terminus and the next probe terminus (See, e.g., probes A' and B, of FIGS. 2 and 3.)

By convention in this application, a modified end is referred to herein as a "recess", the recess being the gap between two primary or secondary probes after hybridizing to the target. The presence of these modified ends reduces the falsely positive signal created by blunt-end ligation of complementary probe duplexes to one another in the absence of target.

"Correction" of the modification is subsequently carried out to render the probes ligatable. As used herein "correction" refers to the process of rendering in a target dependent manner, the two primary probes or the two secondary probes ligatable to their partners. Thus, only those probes hybridized to target, target complement or polynucleotide sequences generated therefrom are "corrected." "Correction" can be accomplished by several procedures, depending on the type of modified end used.

As used herein, "point of ligation" or "intended point of ligation" refers to a specific location between two probe partners that are to be ligated in a template-dependent manner. It is the site at which the "corrected" probe lies adjacent its partner in 3' hydroxyl-5' phosphate relationship. For each set of four LCR probes there are two "points of ligation", a point for the primary probe partners and a point for the secondary probe partners. In conventional LCR the two points of ligation are opposite one another, thus forming blunt ended duplexes when the probe pairs hybridize to one another. In the present invention, the points of ligation are not opposite one another; but are displaced from one another in the "recess" embodiments by one or more bases by virtue of the gaps. The exact point(s) of ligation varies depending on the embodiment and, thus, this term is further defined in the context of each embodiment.

Each of the probes may comprise deoxyribonucleic acid (DNA) or ribonucleic acid (RNA). It is a routine matter to synthesize the desired probes using conventional nucleotide phosphoramidite chemistry and the instruments available from Applied Biosystems, Inc, (Foster City, Calif.); DuPont, (Wilmington, Del.); or Milligen, (Bedford, Mass.). Phosphorylation of the 5' ends of the appropriate probes (eg. A' and B), while necessary for ligation by ligase, may be accomplished by a kinase or by commercial synthesis reagents, as is known in the art.

Throughout this application, the bases X, Y and Q, and their complements are described as being selected from certain subsets (N or M) of the 4 bases. In reality, the sequences are not "selected" at all, but are dictated by the sequence of the target strand. The term "selected" in this context is taken to mean that a target sequence having the desired characteristics is located and probes are constructed around an appropriate segment(s) of the target sequence.

In general, the methods of the invention comprise repeated steps of (a) hybridizing the modified probes to the target (and, if double stranded so that target complement is present, to the target complement); (b) correcting the modification in a target dependent manner to render the probes ligatable; (c) ligating the corrected probe to its partner to form a fused or ligated product; and (d) dissociating the fused product from the target and repeating the hybridization, correction and ligation steps to amplify the desired target sequence. Steps (a), (c) and (d) are essentially the same for all of the embodiments and can be discussed together. They are generally the same steps that one would employ in conventional LCR. Step (b) varies depending on the type of modification employed and each different type is discussed separately.

Hybridization of probes to target (and optionally to target complement) is adequately explained in the prior art; e.g EP-320 308. Probe length, probe concentration and stringency of conditions all affect the degree and rate at which hybridization will occur. Preferably, the probes are sufficiently long to provide the desired specificity; i.e, to avoid being hybridizable to nontarget sequences in the sample. Typically, probes on the order of 15 to 100 bases serve this purpose. Presently preferred are probes having a length of from about 15 to about 40 bases.

The probes are added in approximately equimolar concentration since they are expected to react stoichiometrically. Each probe is present in a concentration ranging from about 5 nanomolar (nM) to about 90 nM; preferably from about 10 nM to about 35 nM. For a standard reaction volume of 50 μL, this is equivalent to adding from about $3 \times 10^{11}$ to about $1 \times 10^{12}$ molecules of each probe; and around $5 \times 10^{11}$ molecules per 50 μL has been a good starting point. The optimum quantity of probe used for each reaction also varies depending on the number of cycles which must be performed and, of course, the reaction volume. Probe concentrations can readily be determined by one of ordinary skill in this art to provide optimum signal for a given number of cycles.

The stringency of conditions is generally known to those in the art to be dependent on temperature, solvent and other parameters. Perhaps the most easily controlled of these parameters is temperature and thus it is generally the stringency parameter varied in the performance of LCR. Since the stringency conditions required for practicing this invention are not unlike those of ordinary LCR, further detail is deemed unnecessary, the routine practitioner being guided by the examples which follow.

The next step in the general method follows the specific correction step and comprises the ligation of one probe to its adjacent partner. Thus, each corrected primary probe is ligated to its associated primary probe and each corrected secondary probe is ligated to its associated secondary probe. An "adjacent" probe is either one of two probes hybridizable with the target in a contiguous orientation, one of which lies with its phosphorylated 5' end in abutment with the 3' hydroxyl end of the partner probe. "Adjacent" probes are created upon correction of the modified end(s) in a target dependent manner. Since enzymatic ligation is the preferred method of covalently attaching two adjacent probes, the term "ligation" will be used throughout the application. However, "ligation" is a general term and is to be understood to include any method of covalently attaching two probes. One alternative to enzymatic ligation is photo-ligation as described in EP-A-324 616.

The conditions and reagents which make possible the preferred enzymatic ligation step are generally known to those of ordinary skill in the art and are disclosed in the references mentioned in background. Ligating reagents useful in the present invention include T4 ligase, and prokaryotic ligases such as *E coli* ligase, and *Thermus thermophilus* ligase (e.g., ATCC 27634) as taught in EP-320 308. This latter ligase is presently preferred for its ability to maintain activity during the thermal cycling of LCR. Absent a thermally stable ligase, the ligase must be added again each time the cycle is repeated. Also useful are eukaryotic ligases, including DNA ligase of Drosophilia, reported by Rabin, et al., *J. Biol. Chem.* 261:10637–10647 (1986).

Once ligated, the fused, reorganized probe is dissociated (e.g. melted) from the target and, as with conventional LCR, the process is repeated for several cycles. The number of repeat cycles may vary from 1 to about 100, although from about 15 to about 70 are preferred presently.

It is desirable to design probes so that when hybridized to their complementary (secondary) probes, the ends away from the point of intended ligation are not able themselves to participate in other unwanted ligation reactions. Thus, ligatable sticky or blunt ends should be avoided. If such ends must be used, then 5' terminal phosphates should be avoided, eliminated or blocked. This can be accomplished either through synthesizing oligonucleotide probes (which normally carry no 5' terminal phosphate groups), or through the use of phosphatase enzymes to remove terminal phosphates (e.g. from oligonucleotides generated through restriction digests of DNA). Alternatively, ligation of the "wrong" outside ends of the probes can be prevented by blocking the end of at least one of the probes with a "hook" or marker moiety as will be described in detail below. In the absence of one of the above techniques, the outside ends of the probes can be staggered so that if they are joined, they will not serve as template for exponential amplification.

Following amplification, the amplified sequences can be detected by a number of conventional ways known in the art. Typically, detection is performed after separation, by determining the amount of label in the separated fraction. Of course, label in the separated fraction can also be determined subtractively by knowing the total amount of label added to the system and measuring the amount present in the unseparated fraction. Separation may be accomplished by electrophoresis, by chromatography or by the preferred method described below.

In a particularly preferred configuration, haptens, or "hooks", are attached at the available outside ends of at least two probes (opposite ends of fused product), and preferably to the outside ends of all four probes. A "hook" is any moiety having a specific ligand-receptor affinity. Typically, the hook(s) at one end of the fused product (e.g. the 5' end of A and the 3' end of A') comprises an antigen or hapten capable of being immobilized by a specific binding reagent (such as antibody or avidin) coated onto a solid phase. The hook(s) at the other end (e.g. the 3' end of B and the 5' end of B') contains a different antigen or hapten capable of being recognized by a label or a label system such as an antibody-enzyme conjugate. Exemplary hooks include biotin, fluorescein and digoxin among many others known in the art. A substrate is then added which is converted by the enzyme to a detectable product. EP-A-330 221 to Enzo describes oligonucleotides having a biotin molecule attached at one end.

ENDS MODIFIED BY RECESSES

In this embodiment, modified ends are created by eliminating from one or more of the probes a short sequence of bases, thereby leaving a recess or gap between the 5' end of one probe and the 3' end of the other probe when they are both hybridized to the target (or target complement, or polynucleotide generated therefrom). In order for LCR to amplify the target, the gaps between the probes must be filled in (i.e., the modification must be "corrected"). In a first version, this can be done using a polymerase or a reverse transcriptase and an excess of deoxyribonucleotide triphosphates which are complementary to the target strand opposite the gap.

However, prior to discussing this embodiment in detail, a brief digression on set terminology may be helpful. A set (e.g., S) consists of all the elements contained within the set S. The set "not S" then consists of all the remaining elements of the "Universe" which are not found in S. The "Universe" for purposes of this application consists of the four bases G, C, A and T, or G, C, A and U as described above. The intersection of set S and another set (e.g., R) consists only of those elements which are found in both S and R. Thus, as used in this application, the set "not N and not M" consists of those bases which are present in neither the gap $X_n$ nor the gap $Y_m$. According to this invention, the set "not N and not M" must not be an empty set; i.e at least one base must remain in this set to code for the "stopbase".

Gap Filling by Extension

In accordance with this first version, the invention involves repeated steps of (a) hybridizing the probes to the target (and, if double stranded so that target complement is present, to the target complement); (b) extending at least one probe to fill in at least one gap, designated $X_n$; (c) ligating the extended probe to the adjacent probe to form a fused or ligated product; and (d) dissociating the fused product from the target and repeating the hybridization, extension and ligation steps to amplify the desired target sequence.

In this version, which includes both single gap ("SG") and double gap ("DG") configurations, the "gaps" $X_n$ and $Y_m$ which impart the "modified ends" are "corrected" by extending one or both of the modified probes using a polymerase or a reverse transcriptase. Generally, extension of a probe hybridized to a DNA target is accomplished by a DNA polymerase or a Klenow fragment as is known in the art. In the case of an RNA target, extension is accomplished by a reverse transcriptase. Exemplary reverse transcriptases include those from avian myeloblastosis virus (AMY) and Moloney murine leukemia virus (M-MuLV) generally available to those skilled in the art. Certain DNA polymerases will also recognize RNA as template under certain conditions. It is, of course, preferable to utilize extension reagents which are thermally stable and can withstand the cycling of high temperatures required for LCR. If the extension reagent is not thermally stable, it typically must be re-added at each cycle of LCR. Such thermostable polymerases presently include AmpliTaq ™, (available from Cetus-Perkin Elmer), Thermus polymerase (available from Molecular Biology Resources,Inc. Milwaukee, Wis., "MBR") and recombinant or purified native polymerases from *Thermus aquaticus, Thermus thermophilus* or other species known to be thermostable.

Correction by extension in this manner requires the presence in the reaction mixture of deoxyribonucleotide triphosphates (dNTP's) complementary to the bases of the target in the gap region(s). More specifically, for a gap having the sequence $X_n$, the dNTP's that must be supplied are designated dX'TP wherein X' stands for the complements of each base in the gap $X_n$. The dNTP's are commercially available from a number of sources, including Pharmacia (Piscataway, N.J.) and Bethesda Research Laboratories (Gaithersburg, Md.).

Extension must be terminated precisely at the point of ligation so that the extended probe abuts the adjacent probe and can be ligated to it. "Stopbases" are employed for this purpose, (See FIG. 2). A "stopbase", designated Q', is defined in terms of its complement, Q and is accomplished by omitting from the reaction mixture, dNTP's that are complementary to Q; i.e. by omitting dQ'TP from the reaction mixture. Thus it is seen how the bases for the gap sequence(s) must be selected from a set, N, consisting of only three of the four bases, so that the complementary three of the four dNTP's are added to the reaction mixture. When the fourth dNTP, dQ'TP, is absent from the reaction mixture extension will terminate at the desired point of ligation. It follows that Q' is the first base in the adjacent probe, and the base on the target which codes for the stopbase is the first base adjacent the gap (on the 5' end of the $X_n$ gap in FIG. 2).

Figure 2:
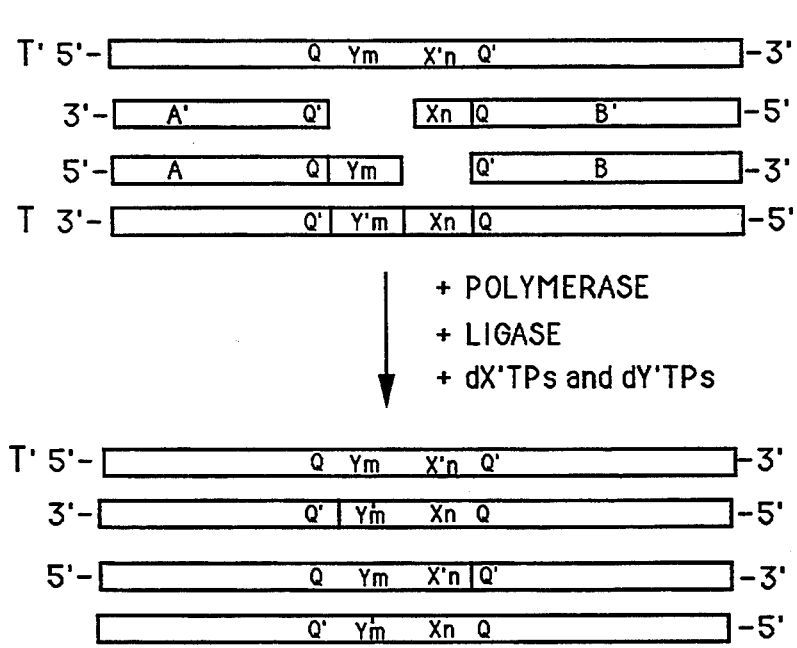
FIG. 2 is a graphic representation of a generalized, double gap variation of the invention.

While the concept is easiest to grasp in the SG configuration, it should be understood that the SG variation is merely a special case of the double gap (DG) variation discussed below (in SG, m=0). However, only the DG configuration is relevant to the presently claimed invention. As shown in FIG. 2, a first probe, A, hybridizes to a first segment of the target strand, T. A second probe, B, hybridizes to a second segment of the target strand, leaving a gap of one or more bases between the two probes This gap is designated $X_n$ on the target. Following extension and ligation, a third probe, A', is hybridizable to a first portion of reorganized probe, A:B; and a fourth probe, B', is hybridizable to a second portion of reorganized probe, A:B. In the DG configuration, the third probe, A', and the fourth probe, B', hybridize such that a gap of one or more bases lies between the probes. This gap is designated $Y_m$ on the reorganized probe (and on target complement). As is shown in FIG. 2, the target strand, T, may be double stranded, having a complement, T'. In this case, the third and fourth probes may participate in the initial hybridization by hybridizing to first and second segments of the target complement.

Extension by polymerase or transcriptase proceeds in a 5' to 3' direction. Consequently, the 3' ends of both A and B'will be extendable by polymerase in the absence of anything to prevent extension. Extension is terminated when the next base called for by the template is absent from the reaction mixture. Thus, probe A is extended through gap $X_n$ until stopbase complement (Q) is encountered along the target strand. Similarly, probe B' is extended through gap $Y_m$ until stopbase complement (Q) is encountered (either on the target complement or on the A half of reorganized A:B). Neither probe A' nor B will serve as a template for extension of A or B', so probes A and B' are extended only if hybridized to the target (or to reorganized polynucleotide products from previous cycles).

As alluded to above, it is important to terminate the extension of A and B' at the end of the respective gaps (i.e., at the point of ligation) so that the extended probe can be ligated to the 5' end of the adjacent probes, B and A'. Therefore, the reaction mixture omits the deoxyribonucleotide triphosphate complementary to the base (Q) immediately adjacent the 5' end of gaps $X_n$ and $Y_m$. Of course, it will be understood that it is not required that the same base stop extension in both directions. A different base can be used provided it is not needed to fill either of the gaps. It should now be apparent that the actual points of ligation in this embodiment are always at the 5' ends of probes A' and B. It is not by mere coincidence that these are also the locations of the stopbases Q'.

Accordingly, the gaps $X_n$ and $Y_m$ can be any number of bases long, i.e., n can be any integer greater than or equal to 1, and m is any integer greater than 0. It is to realized, however, that the choice of which gap is $X_n$ and which is $Y_m$ is arbitrary in the first place; but n and m cannot both be zero. The gaps need not be the same length, i.e., m need not equal n. When, m equals zero, the double gap variation degenerates into the specialized case of the single gap, which is not used in the embodiment being claimed herein. The only restriction on the bases X is that they be selected from a set N which consists of from 1 to any 3 of the four bases. Similarly, the bases Y are drawn from set M. Since at least one stopbase Q' must be maintained, the combined sets N and M which represent the possible bases for X and Y, respectively, must include no more than three of the four bases. Accordingly, Y can be from zero to any three of the four bases provided that at least one base remains in the set "not N and not M". If set N constitutes less than three of the four bases, then Y can be a base that is not within N so long as there is at least one base remaining, the complement of which can serve as the stopbase Q' for termination of probe extension. A single stopbase can serve to terminate extension in both the $X_n$ and $Y_m$ gaps.

A second limitation on sequence $Y_m$ occurs if m equals n. If the gaps are the same length, the sequence $Y_m$ should not be complementary to the sequence $X_n$ or the 3' ends of probes A and B' would constitute "sticky ends". "Sticky ends" would permit a target independent double stranded complex to form wherein probe A hybridizes to probe B' such that ligations and amplification would proceed. Rather, when m equals n it is preferred that $Y_m$ not be complementary to $X_n$. In other words, the ends of probes A and B' should at least be "slippery ends" which may be the same length, but are not complementary.

In a preferred aspect of the invention, the fourth probe B' includes a 3' terminal sequence of $X_n$, identical in length to the $X_n$ sequence gap in the target. This arrangement is not essential to the invention, however, as the gap need only be formed between the probes. Thus, the 3' terminus of the fourth probe B' may stop short of the 3' end of sequence $X_n$, provided there is no 3' recessed end with respect to the second probe B. Since extension occurs in a 5' to 3' direction and dX'TPs must be present anyway (to extend through $X_n$), probe B' would be extended through the gap, (both $Y_m$ and any remainder of $X_n$) just as the first probe A is extended through the $X_n$ gap.

The general method of the invention employing the double gap embodiment is now described briefly. First, probes A, and B are allowed to hybridize to target, if present. If the target is double stranded, it is first denatured and probes A' and B' can also hybridize to the target complement. In the presence of a suitable polymerase, probes A and B' are extended by the addition of dX'TPs and dY'TPs, respectively, to their 3' ends using the target strand as a template. However, when the polymerase encounters the base Q on the template, it is unable further to extend probe A since dQ'TP is not provided in the reaction mixture as dNTP's. Extension terminates precisely at the point of ligation with the extended 3' end of probe A abutting the 5' end of probe B. It is not known if the presence of probes A' and B on the template will terminate extension. But even in their absence, extension is terminated if attention is paid to proper stopbase selection.

Next, a ligase is employed to join the 3' hydroxyl end of extended probe A to the 5' phosphate end of probe B to form a double stranded complex of fused or ligated primary probe and target strand. If the target is double stranded and has a complement T', the ligase will also join probes A' and B' in the initial cycle if they are hybridized to the target complement. If they are hybridized to excess probes A and B rather than target complement, ligation is inhibited since the ends are neither blunt nor sticky and there is no substrate for ligation.

Subsequently, the double stranded complexes are dissociated and new probes A, A', B and B' are permitted to hybridize to the target, the target complement, and both of the fused polynucleotides from the first cycle. Extension and ligation occur as before and the process can be repeated.

Some exemplary combinations of X's and Y's, their dNTP counterparts and the resultant possibilities for Q and Q' are given in Table I.

TABLE I

ILLUSTRATIVE GAP SEQUENCES, REQUIRED dNTPs, and POSSIBLE COMBINATIONS FOR Q and Q' IN DOUBLE GAP VARIATION

| $X_n$/N | $Y_m$/M | X'TPs | Y'TPs | not N and not M* | STOPBASE Q' |
|---|---|---|---|---|---|
| A | A | T | T | T, C, G | A, G, C |
| G | T | C | A | C, A | G, T |
| AT | AT | T, A | T, A | C, G | C, G |
| AC | GA | T, G | C, T | T | A |
| ATG | AAA | T, A, C | T | C | G |
| GGCC | AAACG | C, G | T, G, C | T | A |
| ATTGA | AGGT | T, A, C | T, C, A | C | G |
| CGC | GCG | complement. not permitted | | | |

*The set not N and not M provides the possible complements (Q) for the stopbase Q'. The actual stopbase (Q') possibilities are given in the next column.

In the case of double gaps, the length of gaps $X_n$ and $Y_m$ may be one or any integer greater than one. For example, gaps of from 1 to 20 bases would be possible. Practically, however, gaps of much shorter length are preferred; for example from 1 to 3 or 5 bases. It has been found that gaps of just one or two bases greatly increase the ratio of true signal to background and leave the largest number of options for stopbases and dXTP's. Since probes are actually designed around existing targets, rather than "selecting" stopbases, single or two base gaps are desirable in most cases. Furthermore, it has been discovered that the double gap embodiment is preferred to the single gap version.

TARGET SEQUENCE CHARACTERISTICS

For clarity, double gaps are represented herein as "DG p,q" where "p" is the number of bases in the gap in one strand, and "q" is the number of bases in the gap of the other strand. Thus, a preferred double gap embodiment has two bases missing from each of the two probes whose 5' end participates in the ligation, and is designated DG 2,2. In this preferred embodiment, the 3' ends of the other two probes do not overlap; rather they terminate at the same point on the target strand (and its complement). Also for clarity in this application the use of a dot or period "." between bases in a target sequence represents the point at which the probes, when hybridized to their complementary probes, would be blunt-ended but for the gaps in two of the probes. In other words, probes A and B' (see FIG. 3) have 3' termini which, absent the gaps in probes A' and B, would be blunt-ended at the point of ligation. It is this point at which ligation would have occurred that is designated by a dot. However, with gaps present according to the invention, probes A and B' are extended, thus creating two, offset points of actual ligation.

In a particularly preferred DG embodiment both the gaps are fillable with just one type of deoxyribonucleotide triphosphate. This requires selecting a target sequence having the sequence $-E_p \cdot E'_q$-, where E represents any base, and p and q are integers between 1 and about 10. The probe sets must be designed so that the two probes whose 3' ends participate in the extension/ligation (eg. probes A and B' in FIG. 3) both terminate at the dot "." between E and E'. In order to provide a "stopbase" a further requirement is added. The target sequence must have a base other than E in the next position outward from the E string; and, similarly, must have a base other than E' in the next position outward from the E' string. This can be represented as $-LE_p \cdot E'_q J$-, where L is any base other than E and J is any base other than E'. Finally, to provide sufficient probe length for easy hybridization and, optionally, to provide specificity, the regions $(N)_h$ and $(N)_k$ are employed, to give:

$$5'-(N)_h L E_p \cdot E'_q J (N)_k-3'$$

where N represents any base independently of any other base, N; and h and k are each integers greater than 5. Generally, to provide the desired specificity, the individual probes must be at least 10 or 11 nucleotides long, i.e., the sums (p+h) and (q+k) must be at least 10; more usually will be about 20 to 40, but can be up to 100 or more. As mentioned, p and q may be the same or different, and generally will be small, eg. 1–3.

In this preferred DG 2,2 system, probes would be designed and synthesized as follows, using the designations given in FIG. 3:

A'  Hapten$_1$-3'-(N')$_h$tL'-5'    3'-E$_q$J' (N)$_{kr}$-5'-Hapten$_2$  B'

A   Hapten$_1$-5'-(N)$_h$tL E$_p$-3'    5'-J (N)$_{kr}$-5'-Hapten$_2$  B wherein the terms are defined as above except that h and k need not equal h and k exactly. It is entirely permissible for any of the probes to be slightly shorter or longer than either the target sequence or the complementary probe. This variation in length is indicated by the "  " symbol. The variation is usually no more than 20–25% of the probe length, preferably 10% or less. Of course, no variation in length is also possible. Moreover, h and k may represent a different number at each occurrence, provided they are within the 20–25% variation limit; thus, probe A need not be exactly p bases longer than probe A' (their $(N)_h$ portions may vary in length too) and the same is true for k and probes B and B'.

The single deoxyribonucleotide triphosphate of E' only is needed to fill all the gaps. The bases L and J perform the same function as Q, i.e. to code for the stopbase Q'. However, designations L and J are used here because of the additional restrictions placed on them in this embodiment. As described elsewhere in this specification, haptens 1 and 2 serve to enable separation and detection of ligated products. They are particularly useful for automated detection in the IMx ® instrument (Abbott Laboratories). Hapten 1 should be different than hapten 2. Virtually any low molecular weight compound to which antibodies can be raised may serve as hapten.

Several examples of this preferred embodiment are given in the first column of Table II below and in the Examples which follow.

Another more generalized embodiment of the invention utilizes target sequences and probe sets wherein just two types of deoxyribonucleotide triphosphates are needed to fill all the gaps. Examples of this embodiment are given in the second column of Table II and its target sequence is represented by the following formula:

$$5'-(N)_h X E_p \cdot F_q Z(N)_k-3'$$

wherein N, p, q, h and k are all defined as before. E may be any base as before. F may be any base except E (if it were E the ends would be "sticky" when p=q), but when it is E' this case degenerates to the simpler embodiment described above. Because of the additional flexibility in the choice of F, additional restrictions are placed on the stop bases X and Z. X may be any base but E or F', while Z may be any base but F or E'. The gaps are filled by the deoxyribonucleotide triphosphates of E' and F.

In this DG 2,2 system, probes would be designed and synthesized as follows, using the designations given in FIG. 3:

A'  Hapten$_1$-3'-(N')$_h$tX'-5'    3'-F$_q$Z' (N)$_{kr}$-5'-Hapten$_2$  B'

A   Hapten$_1$-5'-(N)$_h$tX E$_p$-3'    5'-Z (N)$_{kr}$-5'-Hapten$_2$  B

The two deoxyribonucleotide triphosphates needed to fill all the gaps are F and E'. The bases X and Z perform the same function as Q to code for the stop base Q'. However, designations X and Z are used here because of the additional restrictions placed on them in this embodiment. The restrictions are also different than the restrictions on L and J. The haptens are as described above.

It is important the "X" which codes for a stopbase here (or X or X' used in a probe) should not be confused with the $X_n$ gap or the dX'TPs needed to fill the $X_n$ gap. Regrettably, there are only twenty-six letters in the alphabet and most have been used in this application. It is believed that confusion between the two uses of X and X' is avoided by the context.

Other variations of this invention include DG configurations other than 2,2. As shown in Table II and in the examples, DG 1,1; DG 1,2(as well as 2,1);DG 2,3(as well as 3,2) and DG 3,3 are also possible. In addition, gaps of up to 10 bases are included in the generic p and q case, although Table III below shows the low probability of gap junctions longer than about 3. There may be some advantage to having p be approximately equal to q (i.e. varying by only 1 or 2), but this is not a strict requirement. Though not tested, there is no reason to believe a double gap of 1,3 or 2,4 will not also work in the invention.

The above discussion describes in detail the "Special" symbols used in Table II. The "Conventional" symbols will not need further explanation to those of ordinary skill in the art.

TABLE II

EXEMPLARY SINGLE and TWO dNTP FILL DOUBLE GAP ("DG") JUNCTIONS
(The dot "." serves only to align sequences in the Table and to divide
between right and left probe sets: All targets are written
with their 5' end to the left.)

| | Gaps fillable with just one deoxyribonucleotide triphosphate type | | Gaps fillable with just two deoxyribonucleotides triphosphates types | |
|---|---|---|---|---|
| DG 1,1 Generic: | $(N)_h$LE.E'J$(N)_k$ E' fills (in all generic cases) | | $(N)_h$XE.FZ$(N)_k$ E' & fill (in all generic cases) | |
| Subgeneric: | $(N)_h$DC.GH$(N)_k$ | G fills | $(N)_h$KC.TM$(N)_k$ | G & T fill |
| | $(N)_h$HG.CD$(N)_k$ | C fills | $(N)_h$YG.TR$(N)_k$ | C & T fill |
| | $(N)_h$BA.TV$(N)_k$ | T fills | $(N)_h$RC.AY$(N)_k$ | G & A fill |
| | $(N)_h$VT.AB$(N)_k$ | A fills | $(N)_h$MG.AK$(N)_k$ | C & A fill |
| DG 1,2 and 2,1 | $(N)_h$LE.E'E'J$(N)_k$ | | $(N)_h$XE.FFZ$(N)_k$ | |
| Subgeneric: | $(N)_h$DC.GGH$(N)_k$ | G fills | $(N)_h$KC.TTM$(N)_k$ | G & T fill |
| | $(N)_h$HG.CCD$(N)_k$ | C fills | $(N)_h$KCC.TM$(N)_k$ | G & T fill |
| | $(N)_h$BA.TTV$(N)_k$ | T fills | $(N)_h$YG.TTR$(N)_k$ | C & T fill |
| | $(N)_h$VT.AAB$(N)_k$ | A fills | $(N)_h$YGG.TR$(N)_k$ | C & T fill |
| | | | $(N)_h$RC.AAY$(N)_k$ | G & A fill |
| | | | $(N)_h$RCC.AY$(N)_k$ | G & A fill |
| | | | $(N)_h$MG.AAK$(N)_k$ | C & A fill |
| | | | $(N)_h$MGG.AK$(N)_k$ | C & A fill |
| DG 2,2 Generic: | $(N)_h$LEE.E'E'J$(N)_k$ | | $(N)_h$XEE.FFZ$(N)_k$ | |
| Subgeneric: | $(N)_h$DCC.GGH$(N)_k$ | G fills | $(N)_h$KCC.TTM$(N)_k$ | G & T fill |
| | $(N)_h$HGG.CCD$(N)_k$ | C fills | $(N)_h$YGG.TTR$(N)_k$ | C & T fill |
| | $(N)_h$BAA.TTV$(N)_k$ | T fills | $(N)_h$RCC.AAY$(N)_k$ | G & A fill |
| | $(N)_h$VTT.AAB$(N)_k$ | A fills | $(N)_h$MGG.AAK$(N)_k$ | C & A fill |
| DG 2,3 and 3,2 | $(N)_h$LEE.E'E'E'J$(N)_k$ | | $(N)_h$XEE.FFFZ$(N)_k$ | |
| Subgeneric: | $(N)_h$DCCC.GGH$(N)_k$ | G fills | $(N)_h$KCCC.TTM$(N)_k$ | G & T fill |
| | $(N)_h$HGGG.CCD$(N)_k$ | C fills | $(N)_h$KCC.TTTM$(N)_k$ | G & T fill |
| | $(N)_h$BAAA.TTV$(N)_k$ | T fills | $(N)_h$YGGG.TTR$(N)_k$ | C & T fill |
| | $(N)_h$VTTT.AAB$(N)_k$ | A fills | $(N)_h$YGG.TTTR$(N)_k$ | C & T fill |
| | | | $(N)_h$RCCC.AAY$(N)_k$ | G & A fill |
| | | | $(N)_h$RCC.AAAY$(N)_k$ | G & A fill |
| | | | $(N)_h$MGGG.AAK$(N)_k$ | C & A fill |
| | | | $(N)_h$MGG.AAAK$(N)_k$ | C & A fill |
| DG 3,3 Generic: | $(N)_h$LEEE.E'E'EJ$(N)_k$ | | $(N)_h$XEEE.FFFZ$(N)_k$ | |
| Subgeneric: | $(N)_h$DCCC.GGGH$(N)_k$ | G fills | $(N)_h$KCCC.TTTM$(N)_k$ | G & T fill |
| | $(N)_h$HGGG.CCCD$(N)_k$ | C fills | $(N)_h$YGGB.TTTR$(N)_k$ | C & T fill |
| | $(N)_h$BAAA.TTTV$(N)_k$ | T fills | $(N)_h$RCCC.AAAY$(N)_k$ | G & A fill |
| | $(N)_h$VTTT.AAAB$(N)_k$ | A fills | $(N)_h$MGGG.AAAK$(N)_k$ | C & A fill |
| DG p,q | $(N)_h$Lp.E'qJ$(N)_k$ | | $(N)_h$XEp.FqZ$(N)_k$ | |
| GENERAL CASE | | E' alone fills | | E' and F alone fill |

| Where the symbols have the following meanings: | | | |
|---|---|---|---|
| CONVENTIONAL | | SPECIAL | |
| A | Adenine | E | any base |
| B | any base but adenine (not A) | F | any base |
| C | Cytosine | L | any base except E |
| D | any base but cytosine (not C) | J | any base except E' |
| G | Guanine | X | any base except E or F' |
| H | any base but guanine (not G) | Z | any base except F or E' |
| K | G or T/U only | h, k | any integer greater than 1 |
| M | A or C only | p, q | any integer between 1 and about 10 |
| N | any base | | |
| R | A or G only | | |
| S | C or G only | | |
| T | Thymine | | |
| U | Uracil | | |
| V | any base but thymine/uracil | | |
| W | A or T/U only | | |
| Y | C or T/U only | | |

It will be understood that those of ordinary skill in the art will know how to search for and identify specific target sequences meeting the requirements outlined above. For example many databases contain sequence information (eg. GENBANK, NBRF, EMBL or Swiss-Prot) which can be searched by readily available computer software (eg. MacVector, MacMolly or Geneworks). It will also be realized that in any organism's known genome, multiple locations meeting the requirements will generally be found. For example, searching just the SF2CG isolate of HIV 1 (see Examples 1-5), which contains approximately 9.7 kilobases, reveals over 2000 possible DG locations. The breakdown for each type of gap and fill situation is given in Table III. It should be realized that when p=q, a DG p,q on one strand at one location also comprises a DG p,q site on the opposite strand. In the situation where F=E' (i.e. a single dNTP fill) the two target sites are really just one location. Thus, for all symmetric double gaps (where p=q) the Table reports half the number actually found by searching. In contrast, an asymmetric DG (e.g, a DG 1,2 or DG 2,3) on one strand represents a second, different site (but DG 2,1 or DG 3,2, this time) on the opposite strand. Thus, asymmetric sites are reported in the Table without halving the number.

the target strand and be covalently bonded to the adjacent base.

TABLE III

Representative Numbers of Gaps by type in an Organism's Genomic DNA

| Type of GAP | Gaps fillable with just one deoxyribo-nucleotide triphosphate type | Gaps fillable with just two deoxyribo-nucleotide triphosphates types |
|---|---|---|
| HIV 1 (SF 2CG Isolate)[1] (9.7 kb) | | |
| DG 1,1 | 1053 | 1099 |
| DG 1,2 | 538 | 636 |
| DG 2,2 | 75 | 71 |
| DG 2,3 | 42 | 43 |
| DG 3,3 | 8 | 5 |
| C. trachomatis MOMP[2] (2.2 kb) | | |
| DG 1,2 | 120 | 136 |
| DG 2,2 | 24 | 18 |
| DG 2,3 | 8 | 10 |
| DG 3,3 | 0 | 0 |
| C. trachometis cryptic plasmid[3] (7.5 kb) | | |
| DG 1,2 | 415 | 488 |
| DG 2,2 | 61 | 55 |
| DG 2,3 | 39 | 24 |
| DG 3,3 | 6 | 6 |

[1]Sanchez-Pescado, R., et al. Science 227: 484–492 (1985), see examples 1–5.
[2]Baehr, W. et al. Proc. Natl. Acad. Sci. USA 85: 4000–4004 (1988) [EMBL Genbank Data Base: Intelligenetics, Accession #J038 13], see examples 11–12.
[3]Hatt, C. et al. Nuc. Acids Res. 16: 4053–4067 (1988), see example 13.

For the HIV 1 isolate, thirteen of the 75 DG 2,2 single dNTP fill sites are located within the gag region. These 13 locations are listed in Appendix A.

In cases where genomic sequences are not known, at least certain portions must be established prior to using any version of LCR. Typically, one of ordinary skill can determine a sequence through routine methods, such as cloning and sequencing as taught in conventional textbooks on the subject, such as Maniatis, T, et al. *Molecular Cloning: A Laboratory Manual* Cold Spring Harbor Laboratory, Cold Spring Harbor, N.Y. (1982 and 1989).

Whether one is seeking a universal probe set for several types, strains, or serovars, etc. (as might be the case for HIV or Chlamydia), or one is seeking a specific probe set to identify just one type (as might be the case for HPV), one of ordinary skill will know how to compare sequences obtained from such a search with the genomes of other organisms to identify conserved or unique sequences, respectively. In addition, routine laboratory investigations may be needed to confirm the universality or specificity of a particular probe set. The length and nature of $(N)_h$ and $(N)_k$ may greatly affect the universality or specificity of the respective probes, although it is also possible to design probes such that specificity is gained by the gap regions.

Further Features

In a variation of either "recessed" embodiment, the deoxyribonucleotide triphosphates used in filling the gaps may be modified to contain a marker moiety. Exemplary markers include direct labels such as radioisotopes, or hooks such as biotin, digoxin or other hapten capable of being recognized by either a solid phase or a label producing system. Isotopic labels include $^{32}P$, and $^{3}H$ among others.

Incorporation of the marker into the dNTP's is generally a matter of conventional organic chemistry. Linkers or spacers may be used but are not essential. It is only important that the modified dNTP be able to be incorporated into the gap opposite its complement on

EXAMPLES

The invention will now be described further by way of examples which are illustrative of the invention and are not intended to limit it in any way. For example, sequences of specific length are listed. It should be understood that sequences covering the same map positions but having slightly fewer or greater numbers of bases are deemed to be equivalents of these sequences and fall within the scope of the invention, provided they will hybridize to the same positions on the target as the listed sequences.

Figure 3:
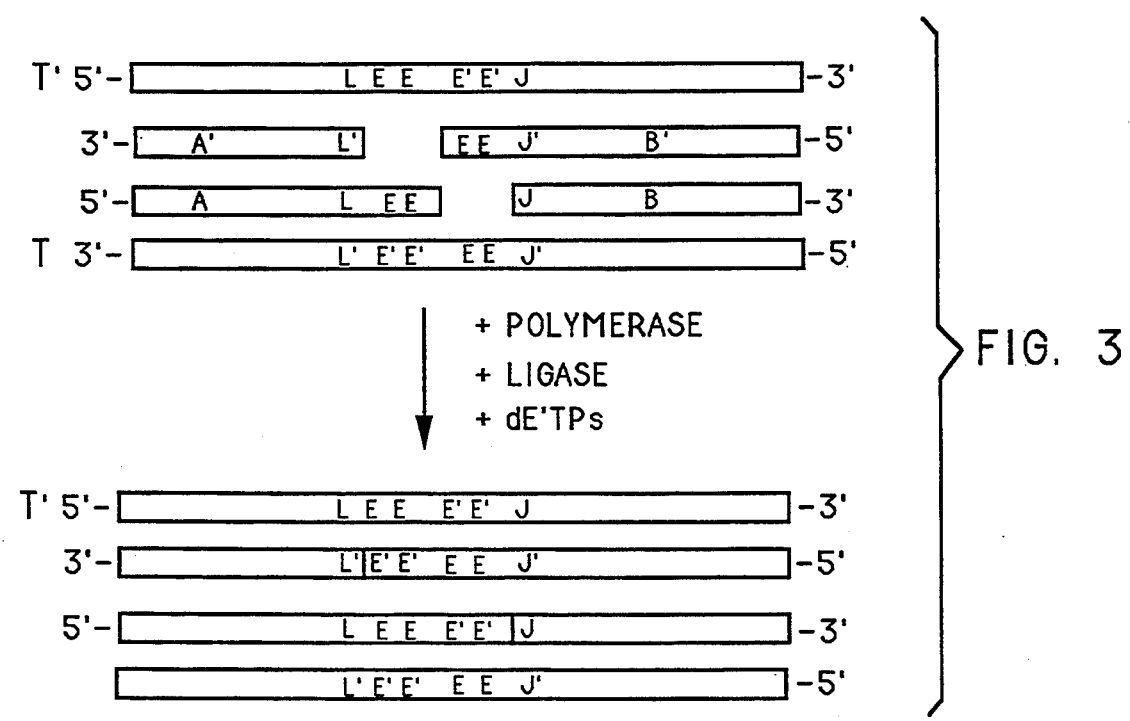
FIG. 3 is a graphic representation of a somewhat more specific double gap variation of the invention.

Unless otherwise indicated, sequences in the examples are written with the 5' end toward the left. In the examples, some probes are labeled with haptens: "FL" represents a fluorescein hapten and "B10" represents a biotin hapten, covalently attached to the probe. The haptens are attached at either the 3' or 5' terminus as shown. Throughout the examples, the numbering system for probes corresponds to a map position followed by a decimal .1, .2, .3, or .4, which correspond to probes A, A', B, B', respectively, of FIG. 3. Thus, arranging the probes as:

.1:.3
.2:.4 yields an arrangement which is upside-down when compared to FIG. 2 or 3. The map position given is for the left-most base when the probes are aligned as if hybridized. The remaining map positions can be calculated from this information, knowing that the left-most position bears the lowest number.

In most of the examples, results were read in an IMx ® instrument. This is commercially available from Abbott Laboratories and is described in EP-A-288 793 and in Fiore, M. et al *Clin. Chem.*, 34/9:1726–1732 (1988). It should be noted that the IMx instrument typically generates "machine" noise or background in the range of 2–8 counts/sec/sec.

Quantities of polymerase are expressed in units, defined (eg., by MBR) as follows: 1 unit of enzyme equals the amount of enzyme required to incorporate 10 nanomoles total nucleotides into acid-insoluble material in 30 min at 70° C. Units of ligase enzyme are defined (internally by Abbott Laboratories) as: 1 mg of 95% purified *Thermus thermophilus* DNA ligase has a specific activity of about $1 \times 10^8$ units. While this is not precisely standardized and may vary by as much as 20%, optimization is within the skill of the routine practitioner.

Examples 1-5 relate to detection of Human Immunodeficiency Virus (HIV1) using several different sequences. The sequences, their map position (SF2CG isolate according to Sanchez-Pescado, R., et al. *Science* 227:484-492 (1985)), and their Sequence ID Nos. are given in Table IV, below. Appendix A gives the number and map positions of DG2,2 targets in the gag region of HIV 1.

human placental DNA. Positive reactions contained the indicated number of copies of HIV1 plasmid DNA in a background of 10 nanograms of placental DNA. The LCR oligonucleotides used are listed in Table IV. These oligonucleotides are specific for the map positions 1667-1716 within the gag region of the HIV1 genome (HIV SF2CG isolate, see Sanchez- Pescado). Reactions were run in a buffer containing 50 mM EPPS pH 7.8, 100 mM KCl, 10 mM $MgCl_2$, 1 mM DTT, 10 mM $NH_4Cl$, 100 μM NAD, 10 μg/ml BSA, $5 \times 10^{11}$ molecules each oligonucleotides 1667.1, 1667.2, 1667.3, 1667.4 (ID Nos. 1-4, respectively), 1 μM 2'-deoxyguanosine 5'-triphosphate, 0.5 units Thermus DNA polymerase (Molecular Biology Resources, Inc., "MBR"), and 3400 units *Thermus thermophilus* DNA ligase. Reaction volume was 50 μl and each reaction was overlaid with 25 μl of mineral oil prior to cycling.

Following amplification, reactions were diluted 1:1

TABLE IV

| MAP POS | SEQUENCE | SEQ ID No. |
|---|---|---|
| 1667.1: | FL-AACCCTTTAG AGACTATGTA GACC | 1 |
| 1667.2: | TCTACATAGT CTCTAAAGGG TTC-FL | 2 |
| 1667.3: | TTCTATAAAA CTCTAAGAGC CGA-BIO | 3 |
| 1667.4: | BIO-CGGCTCTTAG AGTTTTATAG AACC | 4 |
| 912.1: | FL-AGAACGATTC GCAGTCAATC CTGG | 5 |
| 912.2: | AGGATTGACT GCGAATCGTT CTA-FL | 6 |
| 912.3: | TGTTAGAAAC ATCAGAAGGC TGC-BIO | 7 |
| 912.4: | BIO-CAGCCTTCTG ATGTTTCTAA CAGG | 8 |
| 2086.1: | FL-GCTAATTTTT TAGGGAAGAT CTGG | 9 |
| 2086.2: | AGATCTTCCC TAAAAAATTA GCC-FL | 10 |
| 2086.3: | TTCCTACAAG GGAACGCCAG GGA-BIO | 11 |
| 2086.4: | BIO-CCCTGGCGTT CCCTTGTAGG AAGG | 12 |
| 789.1: | FL-GATGGGTGCG AGAGCGTCGG TATT | 13 |
| 789.2: | TACCGACGCT CTCGCACCCA TCT-FL | 14 |
| 789.3: | GCCGGGGGAGA ATTAGATAAA TGG-BIO | 15 |
| 789.4: | BIO-CATTTATCTA ATTCTCCCCC GCTT | 16 |
| 508.1: | FL-ACCCACTGCT TAAGCCTCAA TAAAG | 17 |
| 508.2: | TTTATTGAGG CTTAAGCAGT GGGTT-FL | 18 |
| 508.3: | TTGCCTTGAG TGCTTCAAGT AGTGT-BIO | 19 |
| 508.4: | BIO-CACTACTTGA AGCACTCAAG GCAAG | 20 |
| 5569.1: | FL-GAACAAGCCC CAGAAGACCA AGGG | 21 |
| 5569.2: | TTGGTCTTCT GGGGCTTGTT C-FL | 22 |
| 5569.3: | ACAGAGGGAG CCATACAATG AA-BIO | 23 |
| 5569.4: | BIO-TTCATTGTAT GGCTCCCTCT GTGG | 24 |
| 1450.1: | FL-GCATGCAGGG CCTATTGCAC CAGG | 25 |
| 1450.2: | TGGTGCAATA GGCCCTGCAT G-FL | 26 |
| 1450.3: | AAATGAGAGA ACCAAGGGGA AG-BIO | 27 |
| 1450.4: | BIO-ACTTCCCCTT GGTTCTCTCA TTTGG | 28 |
| 1573.1: | FL-AGAAATCTAT AAAAGATGGA TAAT | 29 |
| 1573.2: | TTATCCATCT.TTTATAGATT TCT-FL | 30 |
| 1573.3: | TGGGATTAAA TAAAATAGTA AG-BIO | 31 |
| 1573.4: | BIO-CTTACTATTT TATTTAATCC CAGG | 32 |
| 4060.1: | FL-GCATTAGGAA TCATTCAAGC ACAA | 33 |
| 4060.2: | GTGCTTGAAT GATTCCTAAT GC-FL | 34 |
| 4060.3: | AGATAAGAGT GAATCAGAGT TA-BIO | 35 |
| 4060.4: | BIO-TAACTCTGAT TCACTCTTAT CTGG | 36 |
| 2683.1: | FL-AAGGAAGGGA AAATTTCAAA AATT | 37 |
| 2683.2: | TTTTTGAAAT TTTCCCTTCC TT-FL | 38 |
| 2683.3: | CCTGAAAATC CATACAATAC T-BIO | 39 |
| 2683.4: | BIO-AGTATTGTAT GGATTTTCAG GCCC | 40 |
| 1753.1: | FL-AACCTTGTTG GTCCAAAATG CAAA | 41 |
| 1753.2: | GCATTTTGGA CCAACAAGGT.T-FL | 42 |
| 1753.3: | AGATTGTAAG ACTATTTTAA A-BIO | 43 |
| 1753.4: | BIO-TTTAAAATAG TCTTACAATC TGGG | 44 |
| 3697.1: | FL-GTAATATGGG GAAAGACTCC TAAA | 45 |
| 3697.2: | AGGAGTCTTT CCCCATATTA C-FL | 46 |
| 3697.3: | AAACTACCCA TACAAAAGGA A-BIO | 47 |
| 3697.4: | BIO-TTCCTTTTGT ATGGGTAGTT TAAA | 48 |

Example 1

Double gap LCR (DG2,2) was performed for 40 cycles consisting of a 65 second incubation at 85° C. and a 65 second incubation at 50° C. Reactions were set up with either 0 or $10^2$ target molecules. The target DNA was a BamH1 fragment of HIV 1 DNA cloned into pBR322. Negative reactions contained 10 nanograms of with IMx diluent buffer, and the LCR amplification products were detected via a sandwich immunoassay performed using the Abbott IMx automated immunoassay system.

| Number of target molecules | Rate |
| --- | --- |
| 0 | 5.76 |
| $10^2$ | 1686.8 |

Example 2

Double gap LCR (DG2,2) was performed for 40 cycles using the same cycling parameters described in Example 1. Reactions were set up in duplicate with either 0, 10 or $10^2$ target DNA molecules. Negative reactions contained 1 microgram of human placental DNA. Positive reactions contained $10^2$ HIV target DNA molecules in 1 microgram of human placental DNA. The oligonucleotides used are listed in Table IV. These oligonucleotides are specific for map positions 912-961 within the gag region of the HIV 1 genome (HIV SF2CG isolate). Reactions were run in a buffer containing 50 mM EPPS pH7.8, 20 mM K+, 30 mM $MgCl_2$, $7.5 \times 10^{11}$ molecules each oligonucleotides 912.1, 912.2, 912.3, 912.4 (ID Nos. 5-8, respectively), 100 µM NAD, 1 µM 2'-deoxycytidine 5'-triphosphate, 0.5 units of Thermus DNA polymerase (MBR), and 3400 units Thermus thermophilus DNA ligase. Reaction volume was 50 µl and each reaction was overlaid with 25 µl of mineral oil.

Following amplification, reactions were diluted 1:1 with IMx diluent buffer and amplification products were detected via a sandwich immunoassay performed with the Abbott IMx automated immunoassay system.

| Number of target molecules | Rate |
| --- | --- |
| 0 | 3.8 |
| 10 | 32.8 |
| $10^2$ | 604.4 |

Example 3

Double gap LCR (DG2,2) was performed for 40 cycles consisting of a 65 second incubation at 85° C. and a 65 second incubation at 60° C. Reactions were set up in quadruplicate with either 0 or $10^2$ HIV 1 target DNA molecules. Negative reactions contained 1 microgram of human placental DNA. Positive reactions contained $10^2$ HIV 1 target DNA molecules in 1 microgram of human placental DNA. The oligonucleotides used are listed in Table IV. These oligonucleotides are specific for map positions 2086-2135 within the gag region of the HIV 1 genome (HIV SF2CG isolate) except that the nucleotide in position 15 of oligonucleotide 2086.3 was changed from G to C to disrupt a possible intramolecular hairpin structure (position 8 in oligonucleotide 2086.4 changed from C to G). Reactions were run in a buffer identical to that used in example 2 except that oligonucleotides 2086.1, 2086.2, 2086.3, and 2086.4 (ID Nos. 9-12, respectively) were used at $7.5 \times 10^{11}$ molecules each per reaction.

Following amplification, reactions were diluted 1:1 with IMx diluent buffer, and the LCR amplification products were detected via a sandwich immunoassay performed using the Abbott IMx automated immunoassay system.

| Number of target molecules | Rate |
| --- | --- |
| 0 | 5.9 |
| $10^2$ | 249.5 |

Example 4

Double gap LCR (DG2,2) was performed for 40 cycles using cycling parameters identical to those used in Example 3. Reactions were set up quadruplicate with either 0 or $10^2$ HIV 1 target DNA molecules. Negative reactions contained 1 microgram of human placental DNA. Positive reactions contained $10^2$ HIV 1 target DNA molecules in 1 microgram of human placental DNA. The oligonucleotides used are listed in Table IV. These oligonucleotides are specific for map position 789-838 within the gag region of the HIV 1 genome (HIV SF2CG isolate). Reaction conditions were identical to those in Example 2 except that oligonucleotides 789.1, 789.2, 789.3, and 789.4 at $7.5 \times 10^{11}$ each (ID Nos. 13-16, respectively), and 2-deoxyadenosine 5'-triphosphate at 1 µM were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
| --- | --- |
| 0 | 3.8 |
| $10^2$ | 604.4 |

Example 5

Double gap LCR (DG1,1) was performed for 45 cycles consisting of a 65 second incubation at 85° C. and a 65 second incubation at 65° C. Reactions were set up in duplicate with either 0 or $10^2$ target DNA molecules. Negative reactions contained 10 nanograms of human placental DNA. Positive reactions contained $10^2$ HIV 1 target DNA molecules in 10 nanograms of human placental DNA. The oligonucleotides used are specific for map positions 508-559 within the LTR region of the HIV 1 genome (HIV SF2CG isolate). Reactions were run in a buffer identical to that used in Example 1 except that oligonucleotides 508.1, 508.2, 508.3, and 508.4 (ID Nos. 17-20, respectively) were used at $5 \times 10^{11}$ molecules each and 2'-deoxycytidine 5'-triphosphate was used at 1 µM.

Following amplification, reactions were diluted 1:1 with IMx diluent buffer, and the LCR amplification products were detected via a sandwich immunoassay performed using the Abbott IMx automated immunoassay system.

| Number of target molecules | Rate |
| --- | --- |
| 0 | 4.5 |
| $10^2$ | 1284.8 |

Example 6

Double gap LCR (DG2,3) is performed for 30-50 cycles as in the previous examples. The oligonucleotides used are listed in Table IV, and are specific for map positions 5569-5616 within the vpu coding region of the HIV 1 genome (HIV SF2CG isolate). Reaction conditions are like those described in Examples 1-3, except that approximately $5 \times 10^{11}$ molecules each of oligonucleotides 5569.1, 5569.2, 5569.3, 5569.4 (ID Nos. 21-24, respectively, and approximately 1 μM 2′-deoxycytidine 5′-triphosphate are used.

Following amplification, the reaction is diluted 1:1 with IMx diluent buffer and amplification products are detected via a sandwich immunoassay performed with the Abbott IMx automated immunoassay system.

Example 7

Double gap LCR (DG2,2) was performed for 45 cycles consisting of a 65 second incubation at 90° C. and a 65 second incubation at 65° C. Reactions were set up in duplicate with either 0 or $10^2$ HIV 1 target DNA molecules. Negative reactions contained 10 nanograms of human placental DNA. Positive reactions contained $10^2$ HIV 1 target molecules in 10 nanograms of placental DNA. The oligonucleotides used are listed in Table IV. These oligonucleotides are specific for map positions 1450-1498 within the gag region of the HIV 1 genome (HIV SF2CG isolate). Reactions were run in a buffer identical to that described in Example 2 except that $5 \times 10^{11}$ molecules each of oligonucleotides 1450.1, 1450.2, 1450.3, and 1450.4 (ID Nos. 25-28, respectively) were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
| --- | --- |
| 0 | 4.8 |
| 102 | 1932.5 |

Example 8

Double gap LCR (DG2,1:2 dNTPs) is performed for 30-50 cycles as in the previous examples. The oligonucleotides used are listed in Table IV, and are specific for map positions 1573-1620 within the gag region of the HIV 1 genome (HIV SF2CG isolate). Reaction conditions are similar to those described in Examples 1-3, except that approximately $5 \times 10^{11}$ molecules each of oligonucleotides 1573.1, 1573.2, 1573.3, 1573.4 (ID Nos. 29-51, respectively), and approximately 1 μM each 2′-deoxycytidine 5′-triphosphate and 2′-deoxyadenosine 5′-triphosphate are used.

Following amplification, reaction is diluted 1:1 with IMx diluent buffer and amplification products are detected via a sandwich immunoassay performed with the Abbott IMx automated immunoassay system.

Example 9

Double gap LCR (DG2,2:2 dNTPs) are performed for 30-50 cycles as in the previous examples. The oligonucleotides used are listed in Table IV, and are specific for map positions 4060-4107 within the pal region of the HIV 1 genome (HIV SF2CG isolate). Reaction conditions are similar to those described in Examples 1-3, except that approximately $5 \times 10^{11}$ molecules each of oligonucleotides 4060.1, 4060.2, 4060.3, 4060.4, (ID Nos. 33-36, respectively) and approximately 1 μM each 2′-deoxythymidine 5′-triphosphate and 2′-deoxycytidine 5′-triphosphate are used.

Following amplification, reaction are diluted 1:1 with IMx diluent buffer and amplification products are detected via a sandwich immunoassay performed with the Abbott IMx automated immunoassay system.

Example 10

Double gap LCR (DG3,2:2 dNTPs) is performed for 30-50 cycles as in the previous examples. The oligonucleotides used are listed in Table IV, and are specific for map positions 2683-2730 within the gag region of the HIV 1 genome (HIV SF2CG isolate). Reaction conditions are similar to those described in Examples 1-3, except that approximately $5 \times 10^{11}$ molecules each of oligonucleotides 2683.1, 2683.2, 2683.3, 2683.4, (ID Nos. 37-40, respectively), and approximately 1 μM each 2′-deoxyadenosine 5′-triphosphate and 2′-deoxyguanosine 5′-triphosphate are used.

Following amplification, reaction is diluted 1:1 with IMx diluent buffer and amplification products are detected via a sandwich immunoassay performed with the Abbott IMx automated immunoassay system.

Example 11

Double gap LCR (DG3,3:2 dNTPs) is performed for 30-50 cycles using the oligonucleotides listed in Table IV. These oligonucleotides are specific for map positions 1753-1800 within the gag region of the HIV 1 genome (HIV SF2CG isolate). Reaction conditions are similar to those described in Examples 1-3, except that approximately $5 \times 10^{11}$ molecules each of oligonucleotides 1753.1, 1753.2, 1753.3, 1753.4 (ID Nos. 41-44, respectively), and approximately 1 μM 2′-deoxythymidine 5′-triphosphate and 2′-deoxycytidine 5′-triphosphate are used.

Following amplification, reaction is diluted 1:1 with IMx diluent buffer and amplification products are detected via a sandwich immunoassay performed with the Abbott IMx automated immunoassay system.

Example 12

Double gap LCR (DG3,3) is performed for 30-50 cycles as in the previous examples. The oligonucleotides used are listed in Table IV, and are specific for map positions 3697-3744 within the pol region of the HIV 1 genome (HIV 1SF2CG isolate) except that the nucleotide in position 17 of oligonucleotide 3697.1 was changed from T to C to disrupt a possible intramolecular hairpin structure (position 5 in oligonucleotide 3697.2 changed from A to G). Reaction conditions are like those described in Examples 1-3, except that approximately $5 \times 10^{11}$ molecules each oligonucleotides 3697.1, 3697.2, 3697.3, 3697.4 (ID Nos. 45-48, respectively), and 1 μM 2′-deoxythymidine 5′-triphosphate are used.

Following amplification, the reactions are diluted 1:1 with IMx diluent buffer and amplification products are detected via a sandwich immunoassay performed with the Abbott IMx automated immunoassay system.

Examples 13-15 relate to the detection of HIV 2 DNA. The sequences, their map position according to Franchini, G., et al. *Proc. Natl. Acad. Sci.* 86:2433-2437 (1988), and their Sequence ID Nos. are given in Table V, below.

TABLE V

| MAP POS | SEQUENCE | SEQ ID No. |
| --- | --- | --- |
| 2060.1: | FL-GACAGAGGAC TTGCTGCACC TCAA | 49 |

TABLE V-continued

| MAP POS | SEQUENCE | SEQ ID No. |
|---|---|---|
| 2060.2: | GAGGTGCAGC AAGTCCTCTG TCG-FL | 50 |
| 2060.3: | CTCTCTTTGG AAAAGACCAG TAG-BIO | 51 |
| 2060.4: | BIO-TACTGGTCTT TTCCAAAGAG AGAA | 52 |
| 4661.1: | FL-ATCACCACAG AACAAGAAAT ACAA | 53 |
| 4661.2: | GTATTTCTTG TTCTGTGGTG ATC-FL | 54 |
| 4661.3: | CCTCCAAGCA AAAAATTCAA AAT-BIO | 55 |
| 4661.4: | BIO-TTTTGAATTT TTTGCTTGGA GGAA | 56 |
| 1094.1: | FL-CTATGATATT AATCAAATGC TTAA | 57 |
| 1094.2: | AAGCATTTGA TTAATATCAT AGG-FL | 58 |
| 1094.3: | GTGTGGGCGA CCATCAAGCA GCG-BIO | 59 |
| 1094.4: | BIO-GCTGCTTGAT GGTCGCCCAC ACAA | 60 |

Example 13

Double gap LCR (DG2,2) was performed for 45 cycles using cycling parameters identical to those described in Example 1. Reactions were set up in triplicate with either 0, $10^2$, or $10^3$ target molecules. The target DNA was a segment of HIV 2 genomic DNA cloned into pTZ18. Negative reactions contained 1 microgram of human placental DNA. Positive reactions contained the indicated number of copies of HIV 2 containing plasmid DNA in a background of 1 microgram of human placental DNA. The oligonucleotides used are listed in Table V. These oligonucleotides are specific for map positions 2060-2109 within the gag region of the HIV 2 genome (HIV21SY isolate) except that the nucleotide in position 14 of oligonucleotide 2060.3 was changed from C to A to disrupt a possible intramolecular hairpin structure (position 9 in oligonucleotide 2060.4 changed from G to T). Reactions were run in a buffer identical to that described in Example 2 except that $5 \times 10^{11}$ molecules each oligonucleotides 2060.1, 2060.2, 2060.3, 2060.4 (ID Nos. 49-52, respectively), and 1 μM 2'-deoxythymidine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
|---|---|
| 0 | 8.4 |
| $10^2$ | 318.4 |
| $10^3$ | 789.3 |

Example 14

Double gap LCR (DG2,2) is performed for 30-50 cycles as in the previous examples. The oligonucleotides used are listed in Table V, and are specific for map positions 1094-1143 within the gag region of the HIV 2 genome (HIV21SY isolate). Reaction conditions are like those described in Examples 1-3, except that approximately $5 \times 10^{11}$ molecules each oligonucleotides 1094.1, 1094.2, 1094.3, 1094.4 (ID Nos. 53-56, respectively), and 1 μM 2'-deoxythymidine 5'-triphosphate are used.

Following amplification, the reactions are diluted 1:1 with IMx diluent buffer and amplification products are detected via a sandwich immunoassay performed with the Abbott IMx automated immunoassay system.

Example 15

Double gap LCR (DG2,2) is performed for 30-50 cycles as in the previous examples. The oligonucleotides used are listed in Table V, and are specific for map positions 4661-4710 within the HIV 2 genome (HIV21SY isolate). Reaction conditions are like those described in Examples 1-3, except that approximately $5 \times 10^{11}$ molecules each oligonucleotides 4661.1, 4661.2, 4661.3, 4661.4 (ID Nos, 57-60, respectively), and 1 μM 2'-deoxythymidine 5'-triphosphate are used.

Following amplification, the reactions are diluted 1:1 with IMx diluent buffer and amplification products are detected via a sandwich immunoassay performed with the Abbott IMx automated immunoassay system.

Examples 16-19 relate to detection of Human Papilloma Virus (HPV), types 16 and 18. The sequences and their Sequence ID Nos are given in Table VI. Map positions for type 18 (Examples 8 and 10) are found in Seedorf, K., et al. *Virology* 145:181-185 (1985); while map positions for type 16 are found in Zhang, Y.-X., Morrison, S. G., and H. D. Caldwell, *Nuc. Acids Res.* 18:1061 (1990).

TABLE VI

| MAP POS | SEQUENCE | SEQ ID No. |
|---|---|---|
| 631.1: | FL-TTTAGAGCCC CAAAATGAAA TTCC | 61 |
| 631.2: | AATTTCATTT TGGGGCTCTA AA-FL | 62 |
| 631.3: | TTGACCTTCT ATGTCACGAG-BIO | 63 |
| 631.4: | BIO-CTCGTGACAT AGAAGGTCAA CC | 64 |
| 480.1: | FL-ATAATATAAG GGGTCGGTGG ACC | 65 |
| 480.2: | TCCACCGACC CCTTATATTA T-FL | 66 |
| 480.3: | TCGATGTATG TCTTGTTGCA GA-BIO | 67 |
| 480.4: | BIO-TCTGCAACAA GACATACAT GACC | 68 |
| 488.1: | FL-CAACATAGCT GGGCACTATA GAGG | 69 |
| 488.2: | TCTATAGTGC CCAGCTATGT TG-FL | 70 |
| 488.3: | AGTGCCATTC GTGCTGCAAC C-BIO | 71 |
| 488.4: | BIO-GGTTGCAGCA CGAATGGCAC TGG | 72 |
| 6604.1 | FL-TTTGTTGGGG TAATCAATTA TTTGTT | 73 |
| 6604.2 | CAAATAATTG ATTACCCCAA CAAA-FL | 74 |
| 6604.3 | CTGTGGTTGA TACCACACGC A-BIO | 75 |
| 6604.4 | BIO-TGCGTGTGGT ATCAACCACA GT | 76 |

Example 16

Double gap LCR was performed for 35 cycles using the same cycling parameters described in Example 1. Reactions were set up in with either 0 or $10^2$ target DNA molecules. The target DNA was full length HPV 18 genomic DNA cloned into pGEM3. Negative reactions contained 15 nanograms of calf thymus DNA. Positive reactions contained $10^2$ HPV 18 target DNA molecules in 15 nanograms of calf thymus DNA. The oligonucleotides used are listed in Table VI. These oligonucleotides are specific for map positions 631-676 in the E6/E7 region of the HPV 18 genome[3]. Reactions were run in a buffer identical to that described in Example 1 except that $5 \times 10^{11}$ molecules each oligonucleotides 631.1, 631.2, 631.3, 631.4 (ID Nos. 61-64, respectively) and 1 μM 2'-deoxyguanosine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
|---|---|
| 0 | 6.8 |
| $10^2$ | 166.6 |

Example 17

Double gap LCR (DG2,2) was performed for 35 cycles using reaction conditions identical to those described in Example 3. Reactions were set up in with either 0 or $10^2$ target DNA molecules. The target DNA was full length HPV 16 genomic DNA cloned into pSP65. Negative reactions contained 15 nanograms of calf thymus DNA. Positive reactions contained $10^2$ target HPV 16 DNA molecules in 15 nanograms of calf thymus DNA. The oligonucleotides used are listed in Table VI. These oligonucleotides are specific for map positions 480–526 within the E6/E7 region of the HPV 16 genome. Reactions were run in a buffer identical to that used in Example 1 except that $5 \times 10^{11}$ molecules each oligonucleotides 480.1, 480.2, 480.3, 480.4 (ID Nos. 65–68, respectively), and 1 μM 2'-deoxyguanosine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
| --- | --- |
| 0 | 5.9 |
| $10^2$ | 289.6 |

Example 18

Double gap LCR (DG2,2) was performed for 35 cycles using the same cycling parameters described in Example 1. Reactions were set up in duplicate with either 0 or $10^6$ target DNA molecules. The target DNA was full length HPV 18 genomic DNA cloned into a plasmid. Negative reactions contained 15 nanograms of calf thymus DNA. Positive reactions contained $10^6$ target HPV 18 DNA molecules in 15 nanograms of calf thymus DNA. The oligonucleotides used are listed in Table VI. These oligonucleotides are specific for map positions 488–534 within the E6/E7 region of the HPV 18 genome. Reactions were run in a buffer identical to that described in Example 1 except that $5 \times 10^{11}$ molecules each oligonucleotides 488.1, 488.2, 488.3, 488.4 (ID Nos. 69–72, respectively), and 1 μM 2'-deoxycytidine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
| --- | --- |
| 0 | 7.0 |
| $10^6$ | 978.2 |

Example 19

Double gap LCR (DG1,2) was performed for 40 cycles consisting of a 65 second incubation at 88° C. and an 80 second incubation at 50° C. Reactions were set up in triplicate with either 0, $10^4$, or $10^6$ target molecules. The target DNA was full length viral genomes cloned into various plasmids. All reactions contained 330 nanograms of human placental DNA. Positive reactions contained $10^4$ or $10^6$ molecules of HPV 6, 16, 18, 31, 33, or 61. The oligonucleotides used are listed in Table VI. These oligonucleotides correspond to map positions 6604–6651 in the HPV 16 genome, but do not match this sequence exactly. Nucleotide changes representing consensus between all of the HPV types listed above were introduced during synthesis. Reactions were run in a buffer identical to that described in Example 2 except that $4 \times 10^{12}$ molecules each of oligonucleotides 6604.1, 6604.2, 6604.3, 6604.4 (ID Nos. 73–76 respectively), 18,000 units of *Thermus thermophilus* DNA ligase, 4 units of Thermus DNA polymerase (MBR), 10 μM NAD, and 1.7 μM 2'-deoxyadenosine 5'-triphosphate were used. Reaction volume was 200 μl with no mineral oil overlay.

Following amplification, LCR reaction products were detected via a sandwich immunoassay performed using the Abbott IMx automated immunoassay system.

| No. of target molecules | Rate (c/s/s) | | | | | |
| --- | --- | --- | --- | --- | --- | --- |
| | HPV Type 6 | HPV Type 16 | HPV Type 18 | HPV Type 31 | HPV Type 33 | HPV Type 61 |
| 0 | 6.6 | 6.6 | 6.6 | 6.6 | 6.6 | 6.6 |
| $10^4$ | 355.4 | 31.4 | 15.3 | 66.9 | 78.8 | 7.4 |
| $10^6$ | 2173.7 | 1163.8 | 805.5 | 1439.7 | 1597.8 | 62.1 |

Examples 20–21 relate to detection of Herpes Simplex Virus (HSV). The sequences used, their map position according to McGeoch, D. J. et al. *J. Gen. Virol.* 68:19–38 (1987), and their Sequence ID Nos. are given in Table V.

TABLE VII

| MAP POS | SEQUENCE | SEQ ID No. |
| --- | --- | --- |
| 4751.1: | FL-CCCCCTGTTC TGGTTCCTAA CGG | 77 |
| 4751.2: | GTTAGGAACC AGAACAGTGG GGA-FL | 78 |
| 4751.3: | TCCCCTGCTC TAGATATCCT CT-BIO | 79 |
| 4751.4: | BIO-GAGGATATCT AGAGCAGGGG AGG | 80 |
| 6465.1: | FL-TATGACAGCT TTAGCGCCGT CAG | 81 |
| 6465.2: | TGACGGCGCT AAAGCTGCAT AG-FL | 82 |
| 6465.3: | GAGGATAACC TGGGGTTCCT GAT-BIO | 83 |
| 6465.4: | BIO-TCAGGAACCC CAGGTTATCC TCG | 84 |

Example 20

Double gap LCR (DG2,2) was performed for 60 cycles consisting of a 60 second incubation at 85° C. and a 60 second incubation at 50° C. Reactions were set up in duplicate with either 0 or $10^2$ target DNA molecules. The target DNA was a 4538 bp segment of the HSV 2 genome cloned into pUC19. Negative reactions contained 10 nanograms of human placental DNA. Positive reactions contained $10^2$ HSV 2 plasmid molecules in 10 nanograms of human placental DNA. The oligonucleotides used are listed in Table VII. These oligonucleotides are specific for map positions 4751–4798 within the US4 region of the HSV 2 genome[2]. Reactions were run in a buffer identical to that described in Example 1 except that oligonucleotides 4751.1, 4751.2, 4751.3, and 4751.4 (ID Nos. 77–80, respectively) at $5 \times 10^{11}$ molecules each per reaction, and 1 μM 2'-deoxycytidine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
|---|---|
| 0 | 6.0 |
| $10^2$ | 2096.0 |

Example 21

Double gap LCR (DG1,1) was performed for 60 cycles using cycling parameters identical to those described in Example 1. Reactions were set up in duplicate with either 0 or $10^2$ target DNA molecules. Negative reactions contained 10 nanograms of human placental DNA. Positive reactions contained $10^2$ HSV target DNA molecules in 10 nanograms of human placental DNA. The oligonucleotides used are listed in Table VII. These oligonucleotides are specific for map positions 6465-6512 of the HSV 2 genome. Reactions were run in a buffer identical to that described in Example 1 except that oligonucleotides 6465.1, 6465.2, 6465.3, and 6465.4 (ID Nos. 81-84, respectively) at $5 \times 10^{11}$ each per reaction and 1 µM 2'-deoxycytidine 5'-triphosphate were used.

Following amplification, reactions were diluted 1:1 with IMx diluent buffer, and LCR reaction products were detected via a sandwich immunoassay performed using the Abbott IMx automated immunoassay system.

| Number of target molecules | Rate |
|---|---|
| 0 | 6.0 |
| $10^2$ | 1156.0 |

Examples 22-24 relate to detection of *Chlamydia trachomatis* DNA. The sequences used and their Sequence ID Nos. are given in Table VII. The map positions for the MOMP region (Examples 11 and 12) are according to Baehr, W. et al. *Proc. Natl. Acad. Sci. USA* 85:4000-4004 (1988) [EMBL Genbank Data Base: Intelligenetics, Accession #J03813]; while the map positions for the cryptic plasmid region (Example 13) are according to Hatt, C. et al. *Nuc. Acids Res.* 16:4053-4067 (1988).

TABLE VIII

| MAP POS | SEQUENCE | SEQ ID No. |
|---|---|---|
| 36.1: | FL-TTTTACTTGC AAGACATTCC TCAGG | 85 |
| 36.2: | TGAGGAATGT CTTGCAAGTA AAAGC-FL | 86 |
| 36.3: | ATTAATTGCT ACAGGACATC TTGTC-BIO | 87 |
| 36.4: | BIO-CAAGATGTCC TGTAGCAATT AATGG | 88 |
| 552.1: | GGGAATCCTG CTGAACCAAG | 89 |
| 552.2: | TTGGTTCAGC AGGATTCCC | 90 |
| 552.3: | TTATGATCGA CGGAATTCTG TG | 91 |
| 552.4: | CACAGAATTC CGTCGATCAT AAGG | 92 |
| 6693.1: | FL-GATACTTCGC ATCATGTGTT CC | 93 |
| 6693.2: | AACACATGAT GCGAAGTATC-FL | 94 |
| 6693.3: | AGTTTCTTTG TCCTCCTATA ACG-BIO | 95 |
| 6693.4: | BIO-CGTTATAGGA GGACAAAGAA ACTCC | 96 |

Example 22

Double gap LCR (DG2,2) was performed for 35 cycles using cycling parameters identical to those described in Example 3. Reactions were set up in duplicate with either 0 or $10^2$ target DNA molecules. The target DNA was purified *Chlamydia trachomatis* genomic DNA. Negative reactions contained 330 nanograms of human placental DNA. Positive reactions contained $10^2$ Chlamydia target DNA molecules in 330 nanograms of human placental DNA. The oligonucleotides used are listed in Table VIII. These oligonucleotides are specific for map positions 36-89 within the major outer membrane protein (MOMP) gene. Reactions were run in a buffer identical to that described in Example 2 except that $5 \times 10^{11}$ molecules each oligonucleotides 36.1, 36.2, 36.3, 36.4 (ID Nos. 85-88, respectively) and 1 µM 2'-deoxycytidine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
|---|---|
| 0 | 7.2 |
| $10^2$ | 34.2 |

Example 23

Double gap LCR (DG1,2) was performed for 40 cycles consisting of a 60 second incubation at 85° C. and a 60 second incubation at 59° C. Reactions were set up in duplicate with either 0 or $10^2$ target molecules. Negative reactions contained 330 nanograms of human placental DNA. Positive reactions contained $10^2$ Chlamydia target DNA molecules in 330 nanograms of human placental DNA. The oligonucleotides used are listed in Table VIII. These oligonucleotides are specific for map positions 552-595 within the MOMP gene. Reactions were run in a buffer identical to that described in Example 3 except that $8 \times 10^{11}$ molecules each of oligonucleotides 552.1 552.2 552.3 552.4 (ID Nos. 89-92, respectively), and 1 µM $\alpha^{32}P$ labelled 2'-deoxycytidine 5'-triphosphate are used.

Following amplification, the reaction products were separated by electrophoresis on a 10% polyacrylamide gel with 8.0M urea at 330 V constant for about 2 hours. The gels were then autoradiographed for about 12 hours with intensifying screens (optional). In the presence of target, autoradiography revealed bands equatable with the extended, unligated probe, and the longer, ligated product. The negative control gave no discernable bands.

Example 24

Double gap LCR (DG2,2) was performed for 40 cycles consisting of a 60 second incubation at 85° C. and a 60 second incubation at 59° C. Reactions were set up in duplicate with either 0 or $10^2$ target molecules. Negative reactions contained 330 nanograms of human placental DNA. Positive reactions contained $10^2$ Chlamydia target DNA molecules in 330 nanograms of human placental DNA. The oligonucleotides used are listed in Table VIII. These oligonucleotides are specific for map positions 6693-6739 within the *Chlamydia trachomatis* cryptic plasmid. Reactions were run in a buffer identical to that described in Example 3 except that $8 \times 10^{11}$ molecules each oligonucleotides 6693.1, 6693.2, 6693.3, 6693.4 (ID Nos. 93-96 respectively), and 1 µM 2'-deoxyguanosine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
|---|---|
| 0 | 4.8 |
| 10² | 1538.8 |

Examples 25-29 relate to detection of *Neisseria gonorrhoeae*. The sequences used are given in Table IX. The map positions for the laz region (example 25) are according to Gotschlich, E. C., and M. E. Seiff. *FEMS Microbiol. Letts.* 43:253-255 (1987). The map positions for the P.II/opa region (examples 26 & 27) are according to Stern, A., M. Brown, P. Nickel, and T. F. Meyer. *Cell* 47:61-71 (1986). The map positions for the pilin region (examples 28 & 29) are according to Meyer, T. F., E. Billyard, R. Haas, S. Storzbach, and M. So. *Proc. Natl. Acad. Sci. USA* 81:6110-6114 (1984).

TABLE IX

| MAP POS | SEQUENCE | SEQ ID No. | GENE |
|---|---|---|---|
| 27.1: | FL-AATATTTGCG CGGCGGGGAC GG | 97 | |
| 27.2: | GTCCCCGCCG CGCAAATATT -FL | 98 | laz |
| 27.3: | TGCCCTAATA TTAAAGAAAT AGGTT-BIO | 99 | |
| 27.4: | BIO-AACCTATTTC TTTAATATTA GGGCAG | 100 | |
| 66.1: | FL-GCCATATTGT GTTGAAACAC CGCCC | 101 | |
| 66.2: | CGGTGTTTCA ACACAATATG GC-FL | 102 | opa |
| 66.3: | AACCCGATAT AATCCGCCCT T-BIO | 103 | |
| 66.4: | BIO-AAGGGCGGAT TATATCGGGT TCC | 104 | |
| 114.1: | FL-CAACATCAGTG AAAATCTTTT TTTAACC | 105 | |
| 114.2: | TTAAAAAAAG ATTTTCACTG ATGTTG-FL | 106 | opa |
| 114.3: | TCAAACCGAA TAAGGAGCCG A-BIO | 107 | |
| 114.4: | BIO-TTCGGCTCCT TATTCGGTTT GACC | 108 | |
| 822.1: | FL-TGATGCCAGC TGAGGCAAAT TAGG | 109 | |
| 822.2: | TAATTTGCCT CAGCTGGCAT CA-FL | 110 | pilin[a] |
| 822.3: | TTAAATTTCA AATAAATCAA GCGGTA-BIO | 111 | |
| 822.4: | BIO-TACCGCTTGA TTTATTTGAA ATTTAAGG | 112 | |
| 933.1: | FL-CGGGCGGGGT CGTCCGTTCC | 113 | |
| 933.2: | AACGGACGAC CCCGCCCG-FL | 114 | pilin |
| 933.3: | TGGAAATAAT ATATCGATT-BIO | 115 | |
| 933.4: | BIO-AATCGATATA TTATTTCCAC C | 116 | |

[a]The sequences shown are a consensus of all published *N. gonorrhoeae* pilin genes and when taken in total do not exactly match any one particular sequence.

Example 25

Double gap LCR (DG2,1) was performed for 35 cycles consisting of a 30 second incubation at 85° C. and a 60 second incubation at 54° C. Reactions were set up in duplicate with genomic DNA from the indicated cells. All Neisseria DNA's were tested in the presence of 320 ng human placenta DNA. The oligonucleotides used (see Table IX, above) are specific for map positions 27-74 within the *Neisseria gonorrhoeae* laz gene. Reactions were run in a buffer identical to that described in Example 3 except that $5 \times 10^{11}$ molecules each of oligonucleotides 27.1, 27.2, 27.3, 27.4 (ID Nos. 97-100, respectively), and 1μM 2'-deoxycytidine 5'-triphosphate were used.

Following amplification, reactions were diluted 1:1 with IMx diluent buffer, and the LCR amplification products were detected via a sandwich immunoassay performed using the Abbott IMx automated immunoassay system.

| DNA Source (Amount) | Rate |
|---|---|
| *Neisseria gonorrhoeae* (200 cells) | 576 |
| *Neisseria meningitidis* (2 × 10⁶ cells) | 6 |
| *Neisseria lactamica* (2 × 10⁶ cells) | 5 |
| Human placenta (320 ng) | 5 |

Example 26

Double gap LCR (DG3,2) was performed for 27 cycles consisting of a 30 second incubation at 85° C. and a 60 second incubation at 57° C. Reactions were set up in duplicate with genomic DNA from the indicated cells. All Neisseria DNA's were tested in the presence of 320 ng human placenta DNA. The oligonucleotides used (see Table IX, above) are specific for map positions 66-113 within the *Neisseria gonorrhoeae* opa gene. Reactions were run in a buffer identical to that described in Example 3 except that $5 \times 10^{11}$ molecules each of oligonucleotides 66.1, 66.2, 66.3, 66.4 (ID Nos. 101-104, respectively), and 1 μM 2'-deoxyguanosine 5'-triphosphate were used.

Following amplification, reactions were diluted 1:1 with IMx diluent buffer, and the LCR amplification products were detected via a sandwich immunoassay performed using the Abbott IMx automated immunoassay system.

| DNA Source (Amount) | Rate |
|---|---|
| *Neisseria gonorrhoeae* (200 cells) | 1710 |
| *Neisseria meningitidis* (2 × 10⁶ cells) | 18 |
| *Neisseria lactamica* (2 × 10⁶ cells) | 8 |
| Human placenta (320 ng) | 6 |

Example 27

Double gap LCR (DG2,2) was performed for 35 cycles consisting of a 30 second incubation at 85° C. and a 60 second incubation at 54° C. Reactions were set up in duplicate with genomic DNA from the indicated cells. All Neisseria DNA's were tested in the presence of 320 ng human placenta DNA. The oligonucleotides used (see Table IX, above) are specific for map positions 114-165 within the *Neisseria gonorrhoeae* opa gene. Reactions were run in a buffer identical to that described in Example 3 except that $5 \times 10^{11}$ molecules each of oligonucleotides 114.1, 114.2, 114.3, 114.4 (ID Nos. 105-108, respectively), and 1 μM 2'-deoxyguanosine 5'-triphosphate were used.

Following amplification, reactions were diluted 1:1 with IMx diluent buffer, and the LCR amplification products were detected via a sandwich immunoassay performed using the Abbott IMx automated immunoassay system.

| DNA Source (Amount) | Rate |
|---|---|
| *Neisseria gonorrhoeae* (200 cells) | 306 |
| *Neisseria meningitidis* (2 × 10⁶ cells) | 10 |
| *Neisseria lactamica* (2 × 10⁶ cells) | 10 |
| Human placenta (320 ng) | 9 |

Example 28

Double gap LCR (DG2,2) was performed for 35 cycles consisting of a 30 second incubation at 85° C. and a 60 second incubation at 50° C. Reactions were set up in duplicate with genomic DNA from the indicated cells. All Neisseria DNA's were tested in the presence of 320 ng human placenta DNA. The oligonucleotides used (see Table IX, above) are specific for map positions 822–873 within the *Neisseria gonorrhoeae* pilin gene. Reactions were run in a buffer identical to that described in Example 3 except that 5×10¹¹ molecules each of oligonucleotides 822.1, 822.2, 822.3, 822.4 (ID Nos. 109–112, respectively), and 1 μM 2'-deoxycytidine 5'-triphosphate were used.

Following amplification, reactions were diluted 1:1 with IMx diluent buffer, and the LCR amplification products were detected via a sandwich immunoassay performed using the Abbott IMx automated immunoassay system.

| DNA Source (Amount) | Rate |
|---|---|
| *Neisseria gonorrhoeae* (200 cells) | 1291 |
| *Neisseria meningitidis* (2 × 10⁶ cells) | 27 |
| *Neisseria lactamica* (2 × 10⁶ cells) | 22 |
| Human placenta (320 ng) | 11 |

Example 29

Double gap LCR (DG2,2) is performed for 30–50 cycles as in earlier examples. The oligonucleotides used (see Table IX, above) are specific for map positions 933–973 within the *Neisseria gonorrhoeae* pilin gene. Reactions are run in a buffer identical to that described in Example 3 except that approximately 5×10¹¹ molecules each of oligonucleotides 933.1, 933.2, 933.3, 933.4 (ID Nos. 113–116, respectively), and 1 μM 2'-deoxyguanosine 5'-triphosphate are used.

Following amplification, reactions are diluted 1:1 with IMx diluent buffer, and the LCR amplification products are detected via a sandwich immunoassay performed using the Abbott IMx automated immunoassay system.

Examples 30 and 31 relate to the detection of *Borrelia burgdorferi*, the causative agent of "Lyme" disease. The sequences used, their map position according to Rosa, P. A., and T. G. Schwan. *J. Infect. Dis.* 160:1018–1029 (1989), and their Sequence ID Nos. are given in Table X, below.

TABLE X

| MAP POS | SEQUENCE | SEQ ID No. |
|---|---|---|
| 5.1: | FL-AAAACGAAGA TACTAAATCT GTAA | 117 |
| 5.2: | ACAGATTTAG TATCTTCGTT TT-FL | 118 |
| 5.3: | GCAGAAACAC CTTTTGAATT AA-BIO | 119 |
| 5.4: | BIO-TTAATTCAAA AGGTGTTTCT GCAA | 120 |
| 181.1: | FL-CATCTTTTGG AGCTAAATAT AAG | 121 |
| 181.2: | TTATATTTAG CTCCAAAAGA.TGC-FL | 122 |
| 181.3: | TTGGATTAAC AAAAATAAAC GAT-BIO | 123 |
| 181.4: | BIO-TCGTTTATTT TTGTTAATCC AAG | 124 |

Example 30

Double gap LCR (DG2,2) was performed for 45 cycles consisting of a 25 second incubation at 85° C. and a 70 second incubation at 50° C. Reactions were set up in duplicate with either 0 or 10² target molecules. The target DNA was a random *Borrelia burgdorferi* genomic sequence cloned into pUC18. Negative reactions contained 10 nanograms of calf thymus DNA. Positive reactions contained 10² Borrelia target DNA molecules in 10 nanograms of calf thymus DNA. The oligonucleotides used are listed in Table X, and are specific for map positions 5–53 of the cloned Borrelia genomic DNA. Reactions were run in a buffer identical to that described in Example 1 except that 3× 10¹² molecules each oligonucleotides 5.1 and 5.3 (ID Nos. 117 and 119, respectively), 2×10¹² molecules each oligonucleotides 5.2 and 5.4 (ID Nos. 118 and 120, respectively), 1032 units of *Thermus thermophilus* DNA ligase, and 1 μM 2'deoxythymidine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
|---|---|
| 0 | 6.0 |
| 10² | 152.0 |

Example 31

Double gap LCR (DG1,1) was performed for 45 cycles consisting of a 65 second incubation at 85° C. and a 60 second incubation at 50° C. Reactions were set up in duplicate with either 0 or 10² target molecules. Negative reactions contained 10 nanograms of salmon sperm DNA. Positive reactions contained 10² Borrelia target DNA molecules in 10 nanograms of salmon sperm DNA. The oligonucleotides used are listed in Table X, and are specific for map positions 181–228 of the cloned Borrelia genomic DNA. Reactions were run in a buffer identical to that described in Example 1 except that 1×10¹² molecules each oligonucleotides 181.1, 181.2, 181.3, 181.4 (ID Nos. 121–124, respectively), 500 units of *Thermus thermophilus* DNA ligase, 1.6 units of Thermus DNA polymerase (MBR), and 1 μM 2'-deoxycytidine 5'-triphosphate were used.

Following amplification, reactions were diluted 1:1 with IMx diluent buffer, and the LCR amplification products were detected via a sandwich immunoassay performed using the Abbott IMx automated immunoassay system.

| Number of target molecules | Rate |
|---|---|
| 0 | 5.0 |
| $10^2$ | 319.0 |

The above examples serve to illustrate the invention, but are not intended to limit it in any way, the full scope of the invention being defined by the appended claims.

---

What is claimed is:

1. A method for detecting the presence of a target nucleic acid in a sample, said method employing a ligase chain reaction to create geometrically increasing numbers of reorganized probe molecules in the presence of said target nucleic acid, said method comprising:

a) providing a sample suspected to contain nucleic acid, the nucleic acid having a target sequence of the formula:

$5'\text{-}(N)_h X E_p F_q Z(N)_k\text{-}3'$ or its complement $3'\text{-}(N')_h X' E'_p F'_q Z'(N')_k\text{-}5'$, wherein E represents any base, E' is the complement of E, F represents any base except E, F' is the complement of F, p and q are independently integers from 1 to about 10, X represents any base except E or F', X' is the complement of X, Z represents any base except F or E', Z' is the complement of Z, N represents any base, and h and k are independently integers from 5 to 100, provided (p+h) and (q+k) each are greater than 10, wherein $(N)_h$ and $(N)_k$ represent sequences that are characteristic for the target sought to be detected;

b) providing a plurality of each of four probes having the formulas:

| | |
|---|---|
| $5'-(N)_h X \ E_p-3'$ | A |
| $3'-(N')_h X'-5'$ | A' |
| $5'-Z(N)_k-3'$ | B |
| $3'-F'_q Z'(N')_k-5'$ | B' | wherein N, N', X, X', Z, Z'E, F', h, p, k and q are defined above, except that A and A' or B and B' need not be identical in length, and wherein at least one of the probes is labeled with a moiety capable of detection; and also providing deoxyribonucleotide triphosphates of E' and F, a polymerase reagent and a ligase reagent;

c) performing the following cycle at least once:
  i) mixing said probes with said sample under hybridizing conditions to allow probes to hybridize to the target sequence and its complement if present, or to reorganized probes created therefrom;
  ii) using target sequence or reorganized probes created therefrom as template, extending probe A with said polymerase reagent by adding F deoxyribonucleotide triphosphates to its 3' end, and extending probe B' with said polymerase reagent by adding E' deoxyribonucleotide triphosphates to its 3' end
  iii) ligating extended probe A to probe B, and extended probe B' to probe A', using said ligase reagent to form reorganized probe molecules; and
  iv) providing denaturing conditions to separate said reorganized probe molecules from said template;

d) separating reorganized probe molecules from unreorganized labeled probes; and e) detecting the presence of said labeled probes in the reorganized or unreorganized fraction as a measure of the presence of the target sequence.

2. The method according to claim 1 wherein F is E', whereby step b) requires adding the deoxyribonucleotide triphosphate of only E'.

3. The method according to claim 1 wherein p and q are independently integers between 1 and 3, inclusive.

4. The method according to claim 2 wherein p and q are independently integers between 1 and 3, inclusive.

5. The method according to claim 3 wherein the target sequence is selected from the group consisting of $(N)_h KCTM(N)_k$, $(N)_h YGTR(N)_k$, $(N)_h RCAY(N)_k$, $(N)_h MGAK(N)_k$ $(N)_h KCCTTM(N)_k$, $(N)_h YGGTTR(N)_k$, $(N)_h RCCAAY(N)_k$, $(N)_h MGGAAK(N)_k$ $(N)_h KCCCTTTM(N)_k$, $(N)_h YGGGTTTR(N)_k$, $(N)_h RCCCAAAY(N)_k$, and $(N)_h MGGGAAAK(N)_k$.

6. The method according to claim 3 wherein the target sequence is selected from the group consisting of $(N)_h KCTTM(N)_k$, $(N)_h KCCTM(N)_k$, $(N)_h YGTTR(N)_k$, $(N)_h YGGTR(N)_k$, $(N)_h RCAAY(N)_k$, $(N)_h RCCAY(N)_k$, $(N)_h MGAAK(N)_k$, $(N)_h MGGAK(N)_k$, $(N)_h KCCCTTM(N)_k$, $(N)_h KCCTTTM(N)_k$, $(N)_h YGGGTTR(N)_k$, $(N)_h YGGTTTR(N)_k$, $(N)_h RCCCAAY(N)_k$, $(N)_h RCCAAAY(N)_k$, $(N)_h MGGGAAK(N)_k$, and $(N)_h MGGAAAK(N)_k$.

7. The method according to claim 1 wherein the 5' end of probe A and the 3' end of probe A' are bound to a first hapten.

8. The method according to claim 7 wherein the 3' end of probe B and the 5' end of probe B' are bound to a second hapten differing from said first hapten.

9. The method according to claim 8 wherein the step of separating reorganized probe molecules from unreorganized labeled probes comprises capturing on a solid phase one of said first and second haptens.

10. The method according to claim 9 wherein said step of detecting the presence of said labeled probes comprises analyzing said solid phase for the presence of the other of said first and second haptens.

11. The method according to claim 1 wherein the cycle of step c) is repeated from about 20 to about 60 times.

12. A method for detecting the presence of a target nucleic acid in a sample, said method employing a ligase chain reaction to create geometrically increasing numbers of reorganized probe molecules in the presence of said target nucleic acid, said method comprising:

a) providing a sample suspected to contain nucleic acid, the nucleic acid having a target sequence of the formula:

$5'-(N)_h LE_p E'_q L(N)_k-3'$ or its complement $3'-(N')_h L'E'_p \bar{E}_q J'(N')_k-5'$, wherein E represents any base, E' is the complement of E, p and q are independently integers from 1 to about 10, L represents any base except E, L' is the complement of L, J represents any base except E', J' is the complement of J, N represents any base, and h and k are independently integers from 5 to 100, provided (p+h) and (q+k) each are greater than 10, wherein $(N)_h$ and $(N)_k$ represent sequences that are characteristic for the target sought to be detected;

b) providing a plurality of each of four probes having the formulas:

| | |
|---|---|
| $5'-(N)_h L \ E_p-3'$ | A |
| $3'-(N')_h L'-5'$ | A' |
| $5'-J(N)_k-3'$ | B |
| $3'-E'_q J'(N')_k-5'$ | B' | wherein N, N', L, L', E, E', J, J'h, p, k and q are defined above, except that A and A' or B and B' need not be identical in length, and wherein at least one of the probes is labeled with a moiety capable of detection; and also providing deoxyribonucleotide triphosphates of E', a polymerase reagent and a ligase reagent;

c) performing the following cycle at least once:
  i) mixing said probes with said sample under hybridizing conditions to allow probes to hybridize to the target sequence and its complement if present;
  ii) using target sequence or reorganized probes created therefrom as template, extending probes A and B' with said polymerase reagent by adding E' deoxyribonucleotide triphosphates to their 3' ends
  iii) ligating extended probe A to probe B, and extended probe B' to probe A', using said ligase reagent to form reorganized probe molecules; and iv) providing denaturing conditions to separate said reorganized probe molecules from said template;

d) separating reorganized probe molecules from unreorganized labeled probes; and e) detecting the presence of said labeled probes in the reorganized fraction as a measure of the presence of the target sequence.

13. The method according to claim 12 wherein p and q are independently integers between 1 and 3, inclusive.

14. The method according to claim 12 wherein the target sequence is selected from the group consisting of $(N)_hDCGH(N)_k$, $(N)_hHGCD(N)_k$, $(N)_hBATV(N)_k$, $(N)_hVTAB(N)_k$, $(N)_hDCCGGH(N)_k$, $(N)_hHGGCCD(N)_k$, $(N)_hBAATTV(N)_k$, $(N)_hVTTAAB(N)_k$, $(N)_hDCCCGGGH(N)_k$, $(N)_hHGGGCCCD(N)_k$, $(N)_hBAAATTTV(N)_k$, and $(N)_hVTTTAAAB(N)_k$.

15. The method according to claim 12 wherein the target sequence is selected from the group consisting of $(N)_hDCGGH(N)_k$, $(N)_hHGCCD(N)_k$, $(N)_hBATTV(N)_k$, $(N)_hVTAAB(N)_k$, $(N)_hDCCCGGH(N)_k$, $(N)_hHGGGCCD(N)_k$, $(N)_hBAATTV(N)_k$, and $(N)_hVTTTAAB(N)_k$.

16. The method according to claim 12 wherein at least one probe is labeled with a hapten, and wherein at least one of the steps d and e comprise reacting said hapten with a specific binding reagent for said hapten.

17. A method for determining the presence of HIV 1 in a sample, said method comprising amplifying a target region using at least two probes specific for said region and detecting amplified product, wherein said at least two probes are each selected from a single probe set, said probe set being selected from the group of probe sets consisting of:

at map position 1667, SEQ ID Nos 1, 2, 3 and 4;
at map position 912, SEQ ID Nos. 5, 6, 7 and 8;
at map position 2086, SEQ ID Nos. 9, 10, 11 and 12;
at map position 789, SEQ ID Nos. 13, 14, 15 and 16;
at map position 508, SEQ ID Nos. 17, 18, 19 and 20;
at map position 5569, SEQ ID Nos. 21, 22, 23 and 24;
at map position 1450, SEQ ID Nos. 25, 26, 27 and 28;
at map position 1573, SEQ ID Nos. 29, 30, 31 and 32;
at map position 4060, SEQ ID Nos. 33, 34, 35 and 36;
at map position 2683, SEQ ID Nos. 37, 38, 39 and 40;
at map position 1753, SEQ ID Nos. 41, 42, 43 and 44; and
at map position 3697, SEQ ID Nos. 45, 46, 47 and 48.

18. A method for determining the presence of HIV 2 in a sample, said method comprising amplifying a target region using at least two probes specific for said region and detecting amplified product, wherein said at least two probes are each selected from a single probe set, said probe set being selected from the group of probe sets consisting of:

at map position 2060, SEQ ID Nos 49, 50, 51 and 52;
at map position 4661, SEQ ID Nos. 53, 54, 55 and 56; and
at map position 1094, SEQ ID Nos. 57, 58, 59 and 60.

19. A method for determining the presence of HPV in a sample, said method comprising amplifying a target region using at least two probes specific for said region and detecting amplified product, wherein said at least two probes are each selected from a single probe set, said probe set being selected from the group of probe sets consisting of:

at map position 631, SEQ ID Nos 61, 62, 63 and 64;
at map position 480, SEQ ID Nos 65, 66, 67 and 68;
at map position 488, SEQ ID Nos. 69, 70, 71 and 72; and
at map position 6604, SEQ ID Nos. 73, 74, 75 and 76.

20. A method for determining the presence of HSV in a sample, said method comprising amplifying a target region using at least two probes specific for said region and detecting amplified product, wherein said at least two probes are each selected from a single probe set, said probe set being selected from the group of probe sets consisting of:

at map position 4751, SEQ ID Nos. 77, 78, 79 and 80; and
at map position 6465, SEQ ID Nos. 81, 82, 83 and 84.

21. A method for determining the presence of *Chlamydia trachomatis* in a sample, said method comprising amplifying a target region using at least two probes specific for said region and detecting amplified product, wherein said at least two probes are each selected from a single probe set, said probe set being selected from the group of probe sets consisting of:

at map position 36, SEQ ID Nos 85, 86, 87 and 88;
at map position 552, SEQ ID Nos. 89, 90, 91 and 92; and
at map position 6693, SEQ ID Nos. 93, 94, 95 and 96.

22. A method for determining the presence of *Neisseria gonorrhoeae*, in a sample, said method comprising amplifying a target region using at least two probes specific for said region and detecting amplified product, wherein said at least two probes are each selected from a single probe set, said probe set being selected from the group of probe sets consisting of:

at map position 27, SEQ ID Nos 97, 98, 99 and 100;
at map position 66, SEQ ID Nos 101, 102, 103 and 104;
at map position 114, SEQ ID Nos 105, 106, 107 and 108;
at map position 822, SEQ ID Nos. 109, 110, 111 and 112; and
at map position 933, SEQ ID Nos. 113, 114, 115 and 116.

23. A method for determining the presence of *Borrelia burgdorferi* in a sample, said method comprising amplifying a target region using at least two probes specific for said region and detecting amplified product, wherein said at least two probes are each selected from a single probe set, said probe set being selected from the group of probe Sets consisting of:

at map position 5, SEQ ID Nos. 117, 118, 119 and 120; and
at map position 181, SEQ ID Nos. 121, 122, 123 and 124.

24. A composition of matter useful for detecting HIV 1, said composition comprising a mixture of at least two probes, wherein said at least two probes are each selected from a single probe set, said probe set being selected from the group of probe sets consisting of:

at map position 1667, SEQ ID Nos 1, 2, 3 and 4;
at map position 912, SEQ ID Nos. 5, 6, 7 and 8;
at map position 2086, SEQ ID Nos. 9, 10, 11 and 12;
at map position 789, SEQ ID Nos. 13, 14, 15 and 16;
at map position 508, SEQ ID Nos. 17, 18, 19 and 20;
at map position 5569, SEQ ID Nos. 21, 22, 23 and 24;
at map position 1450, SEQ ID Nos. 25, 26, 27 and 28;
at map position 1573, SEQ ID Nos. 29, 30, 31 and 32;
at map position 4060, SEQ ID Nos. 33, 34, 35 and 36;
at map position 2683, SEQ ID Nos. 37, 38, 39 and 40;

at map position 1753, SEQ ID Nos. 41, 42, 43 and 44; and at map position 3697, SEQ ID Nos. 45, 46, 47 and 48.

25. A composition of matter useful for detecting HIV 2, said composition comprising a mixture of at least two probes, wherein said at least two probes are each selected from a single probe set, said probe set being selected from the group of probe set consisting of:

at map position 2060, SEQ ID Nos 49, 50, 51 and 52;
at map position 4661, SEQ ID Nos. 53, 54, 55 and 56; and
at map position 1094, SEQ ID Nos. 57, 58, 59 and 60.

26. A composition of matter useful for detecting HPV, said composition comprising a mixture of at least two probes, wherein said at least two probes are each selected from a single probe set, said probe set being selected from the group of probe set consisting of:

at map position 631, SEQ ID Nos 61, 62, 63 and 64;
at map position 480, SEQ ID Nos 65, 66, 67 and 68;
at map position 488, SEQ ID Nos. 69, 70, 71 and 72; and
at map position 6604, SEQ ID Nos. 73, 74, 75 and 76.

27. A composition of matter useful for detecting HSV, said composition comprising a mixture of at least two probes, wherein said at least two probes are each selected from a single probe set, said probe set being selected from the group of probe sets consisting of:

at map position 4751, SEQ ID Nos. 77, 78, 79 and 80; and
at map position 6465, SEQ ID Nos. 81, 82, 83 and 84.

28. A composition of matter useful for detecting *Chlamydia trachomatis*, said composition comprising a mixture of at least two probes, wherein said at least two probes are each selected from a single probe set, said probe set being selected from the group of probe sets consisting of:

at map position 36, SEQ ID Nos 85, 86, 87 and 88;
at map position 552, SEQ ID Nos. 89, 90, 91 and 92; and
at map position 6693, SEQ ID Nos. 93, 94, 95 and 96.

29. A composition of matter useful for detecting *Neisseria gonorrhoeae*, said composition comprising a mixture of at least two probes, wherein said at least two probes are each selected from a single probe set, said probe set being selected from the group of probe sets consisting of:

at map position 27, SEQ ID Nos 97, 98, 99 and 100;
at map position 66, SEQ ID Nos 101, 102, 103 and 104;
at map position 114, SEQ ID Nos 105, 106, 107 and 108;
at map position 822, SEQ ID Nos. 109, 110, 111 and 112; and
at map position 933, SEQ ID Nos. 113, 114, 115 and 116.

30. A composition of matter useful for detecting *Borrelia burgdorferi*, said composition comprising a mixture of at least two probes, wherein said at least two probes are each selected from a single probe set, said probe set being selected from the group of probe sets consisting of:

at map position 5, SEQ ID Nos. 117, 118, 119 and 120; and
at map position 181, SEQ ID Nos. 121, 122, 123 and 124.

* * * * *

UNITED STATES PATENT AND TRADEMARK OFFICE
CERTIFICATE OF CORRECTION

PATENT NO. : 5,427,930     Page 1 of 3
DATED : Jun. 27, 1995
INVENTOR(S) : Birkenmeyer et al It is certified that error appears in the above-indentified patent and that said Letters Patent is hereby corrected as shown below:

Column 3, line 7, change "5'-$(N)_h$ X $E_p$-3'" to
--5'-$(N)_{h^\dagger}$ X $E_p$-3'--
Column 3, line 9, change "3'-$(N)_h$ X'-5'" to
--3'-$(N)_{h^\dagger}$X'-5'--.
Column 3, line 11, change "5'-$(N)_k$-3'" to
--5'Z-$(N)_{k^\dagger}$-3'--.
Column 3, line 13, change "3'-$F'_q Z'(N')_k$-5'" to
--3'-$F'_q Z'(N')_{k^\dagger}$-5'--.
Column 3, line 56, change "5'-$(N)_h X E_p . F_p Z(N)_k$-3'" to
--5'-$(N)_h X E_p . F_q Z(N)_k$-3'--.
Column 4, line 1, change "5'-$(N)_h$ X $E_p$-3'" to
--5'-$(N)_{h^\dagger}$ X $E_p$-3'--.
Column 4, line 3, change "3'-$(N')_h$ X-5'" to
--3'-$(N')_{h^\dagger}$X'-5'--.
Column 4, line 5, change "5'-Z$(N)_k$-3'" to
--5'-Z$(N)_{k^\dagger}$-3'--.
Column 4, line 7, change "3+-$F'_q Z'(N')_k$-5'" to
--3'-$F'_q Z'(N')_{k^\dagger}$-5'--.
Column 9, line 27, change "(AMY)" to
--(AMV)--.
Column 13, line 45 & 46, change "h and k" to
--$h^\dagger$ and $k^\dagger$--.
Column 13, line 50, change """" to
--"$^\dagger$"--.
Column 13, line 53, change "h and k" to
--$h^\dagger$ and $k^\dagger$--.
Column 13, line 57, change "$(N)_h$" to
--$(N)_{h^\dagger}$--.
Column 13, line 58, change "k" to
--$k^\dagger$--

UNITED STATES PATENT AND TRADEMARK OFFICE
CERTIFICATE OF CORRECTION

PATENT NO. : 5,427,930  Page 2 of 3
DATED : Jun. 27, 1995
INVENTOR(S) : Birkenmeyer et al.

It is certified that error appears in the above-indentified patent and that said Letters Patent is hereby corrected as shown below:

Column 35, line, change "Insert in Sequence Listing" to
--(i) APPLICANT: Larry G. Birkenmeyer, John J. Carrino, Bruce J. Dille, Hsiang-Yun Hu, Jon David Kratochvil, Thomas G. Laffler, Ronald L. Marshall, Laurie A. Rinehardt, Natalie A. Solomon--.
Column 35, line , change "Insert to Sequence Listing" to
--(ii) TITLE OF INVENTION: AMPLIFICATION OF TARGET NUCLEIC ACIDS USING GAP FILLING LIGASE CHAIN REACTIONS--.
Column 35, line , change "Insert to Sequence Listing" to
--(iv) CORRESPONDENCE ADDRESS: (A) ADDRESSEE: Abbott Laboratories, (B) STREET: 100 Abbott Park Road, (C) CITY: Abbott Park, (D) STATE: Illinois, (E) COUNTRY: USA, (F) ZIP: 60064-3500--.
Column 35, line , change "Insert to Sequence Listing" to
--(v) COMPUTER READABLE FORM: (A) MEDIUM TYPE: Floppy Diskette, (B) COMPUTER: IBM-PC compatible, (C) OPERATING SYSTEM: PC-DOS/MS-DOS, (D) SOFTWARE: Wordperfect 5.0-.
   Column 35, line , change "Insert to Sequence Listing" to
--(vi) CURRENT APPLICATION DATA: (A) APPLICATION NUMBER: 07/ 722,798, (B) FILING DATE: JUNE 28, 1991, (C) CLASSIFICATION:--.

UNITED STATES PATENT AND TRADEMARK OFFICE
CERTIFICATE OF CORRECTION

PATENT NO. : 5,427,930
DATED : Jun. 27, 1995
INVENTOR(S) : Birkenmeyer et al.

It is certified that error appears in the above-indentified patent and that said Letters Patent is hereby corrected as shown below:

Column 81, line 13, add "B'"
Column 82, line 29, change "5'-$(N)_hLE_pE'_qL(N)_k$-3'" to --5'-$(N)_hLE_pE'_qJ(N)_k$-3--.

Signed and Sealed this

Thirty-first Day of December, 1996

Attest:

BRUCE LEHMAN

*Attesting Officer*    *Commissioner of Patents and Trademarks*